(12) United States Patent
Terasawa et al.

(10) Patent No.: US 9,829,442 B2
(45) Date of Patent: Nov. 28, 2017

(54) DEFECT INSPECTING METHOD, SORTING METHOD AND PRODUCING METHOD FOR PHOTOMASK BLANK

(71) Applicant: Shin-Etsu Chemical Co., Ltd., Tokyo (JP)

(72) Inventors: Tsuneo Terasawa, Joetsu (JP); Atsushi Yokohata, Joetsu (JP); Daisuke Iwai, Joetsu (JP); Takahiro Kishita, Joetsu (JP); Hiroshi Fukuda, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/256,111

(22) Filed: Sep. 2, 2016

(65) Prior Publication Data
US 2017/0068158 A1 Mar. 9, 2017

(30) Foreign Application Priority Data

Sep. 4, 2015 (JP) ................................. 2015-174684

(51) Int. Cl.
*G01N 21/00* (2006.01)
*G01N 21/88* (2006.01)
(Continued)

(52) U.S. Cl.
CPC ....... *G01N 21/8851* (2013.01); *G01N 21/956* (2013.01); *G03F 1/84* (2013.01); *G01N 2021/95676* (2013.01)

(58) Field of Classification Search
CPC ................. G01N 21/956; G01N 21/95; G01N 2021/95676; G01N 21/88;
(Continued)

(56) References Cited

U.S. PATENT DOCUMENTS 6,617,603 B2 9/2003 Ishiguro et al.
7,379,176 B2 5/2008 Sekine et al.
(Continued)

FOREIGN PATENT DOCUMENTS

| JP | 2001-174415 A | 6/2001 |
| JP | 2002-333313 A | 11/2002 |

(Continued)

*Primary Examiner* — Michael P Stafira
(74) *Attorney, Agent, or Firm* — Birch, Stewart, Kolasch & Birch, LLP

(57) ABSTRACT

Disclosed is a method of inspecting a defect present at a surface portion of a photomask blank which includes an optical film, and a thin film. The method includes: selecting and designating an inspection treatment procedure and a criterion for determination of rugged shape of the defect which correspond to modes of the optical film and the thin film of the photomask blank; applying inspection light to a region including the defect while maintaining a distance between the defect and an objective lens of an inspecting optical system, based on the designated inspection treatment procedure, and collecting reflected light from the region irradiated with the inspection light, as a magnified image of the region, through the inspecting optical system; and determining the rugged shape of the defect, from light intensity distribution of the magnified image, based on the designated criterion for determination.

18 Claims, 25 Drawing Sheets

(51) Int. Cl.
*G01N 21/956* (2006.01)
*G03F 1/84* (2012.01)

(58) Field of Classification Search
CPC ......... G01N 21/95607; G01N 21/9501; G01N 23/2251; G01N 21/21; G01N 21/211; G01N 21/8851; G01N 21/89; G01N 21/94; G01N 2021/4711; G01N 2021/88
See application file for complete search history.

(56) References Cited

U.S. PATENT DOCUMENTS

| | | | |
|---|---|---|---|
| 7,630,068 B2 | 12/2009 | Tanaka et al. | |
| 2014/0165236 A1* | 6/2014 | Budach | G03F 1/22 850/9 |
| 2015/0079500 A1* | 3/2015 | Shih | G03F 1/80 430/5 |
| 2015/0332922 A1* | 11/2015 | Chien | H01L 21/30625 438/692 |
| 2016/0377553 A1* | 12/2016 | Terasawa | G01B 11/24 430/5 |

FOREIGN PATENT DOCUMENTS

| | | |
|---|---|---|
| JP | 2005-265736 A | 9/2005 |
| JP | 2007-219130 A | 8/2007 |
| JP | 2013-19766 A | 1/2013 |

* cited by examiner

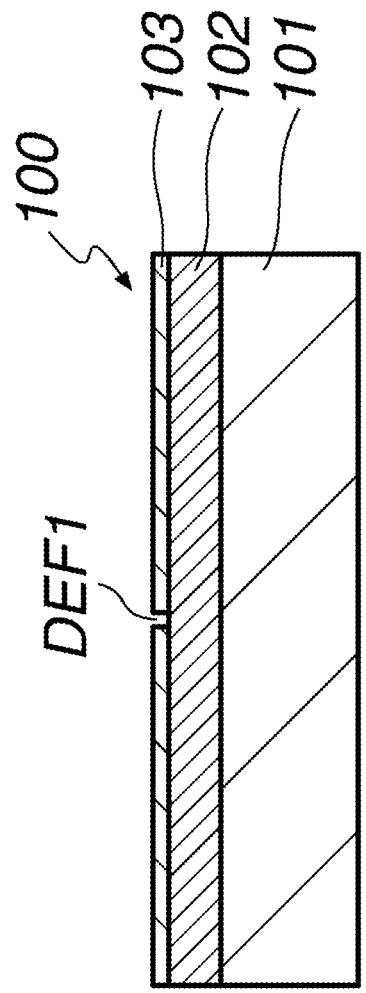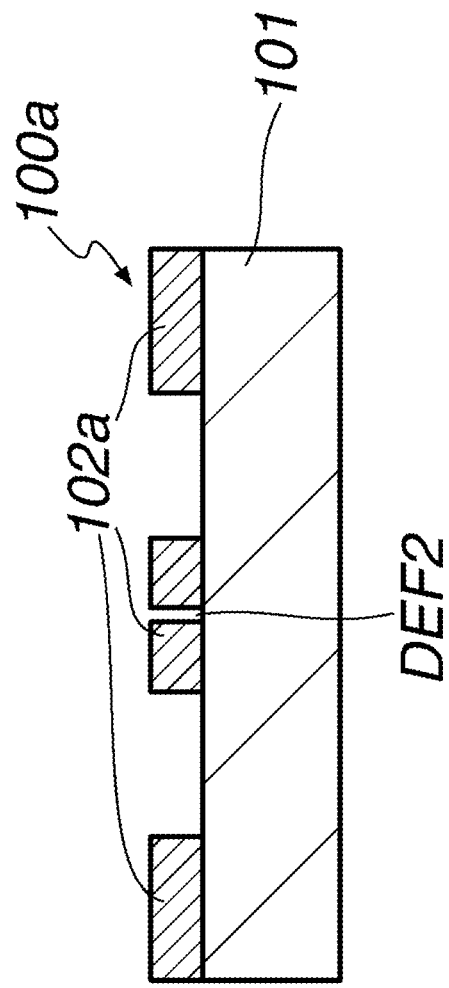

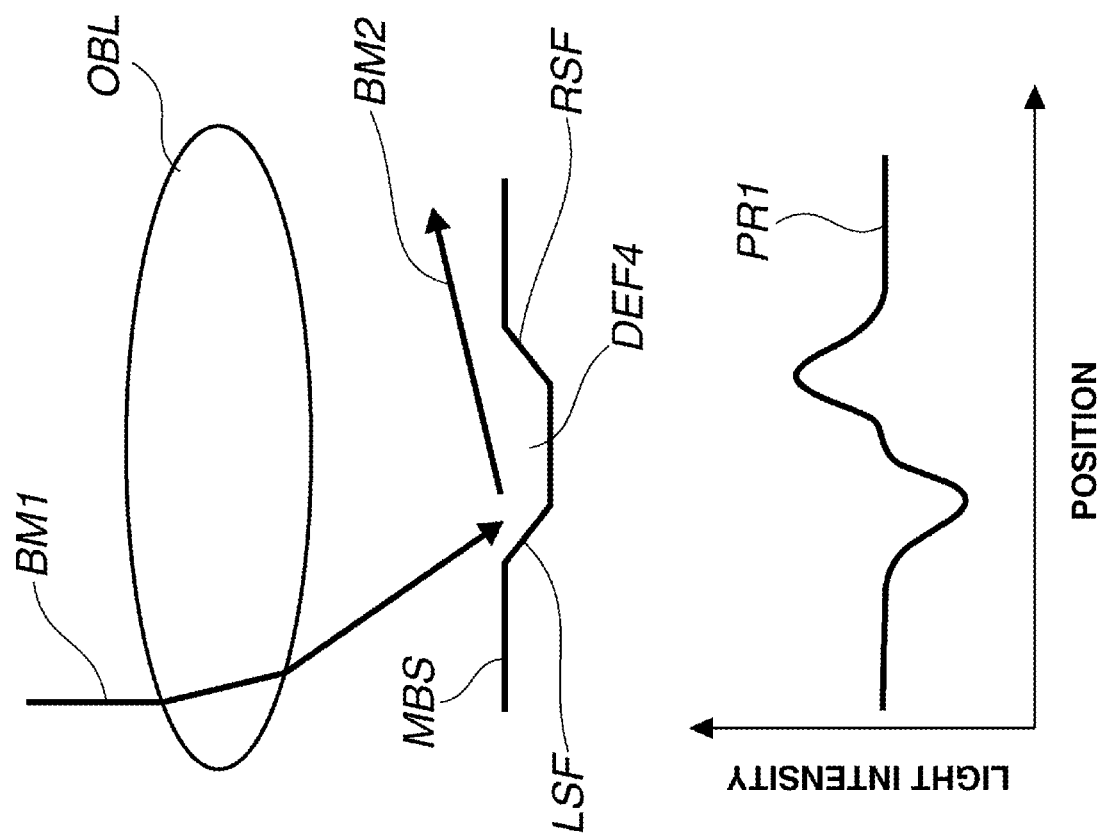

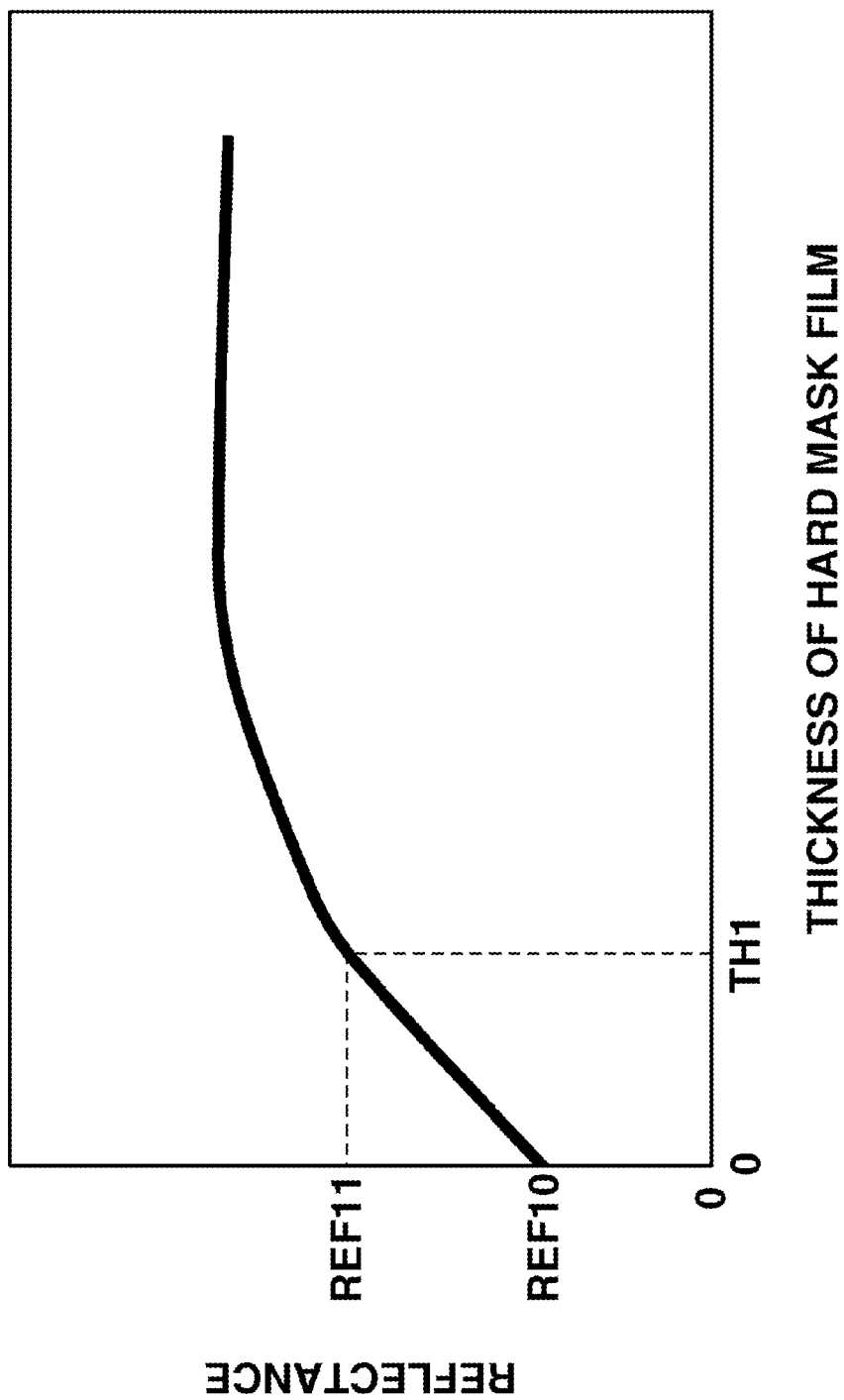

Δz > 0

Δz = 0

Δz < 0

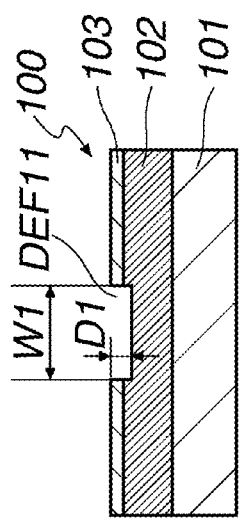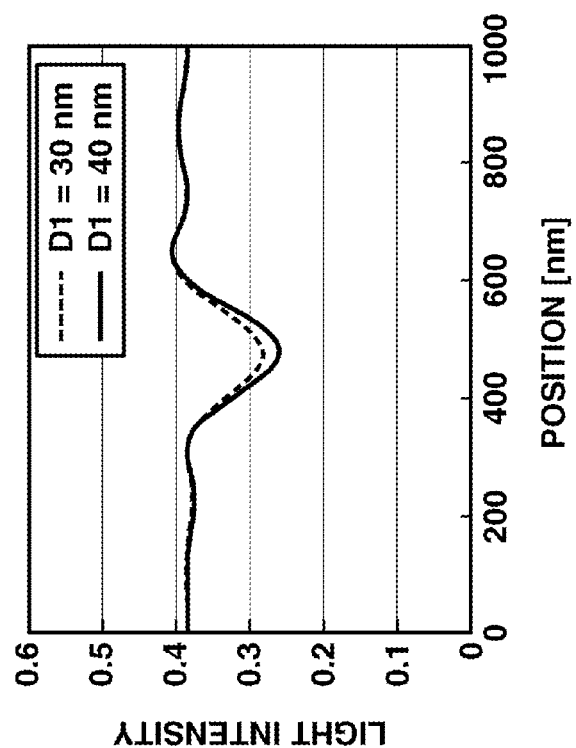
FIG.18A
FIG.18B

Δz = +200 nm

Δz = 0 nm

Δz = −200 nm

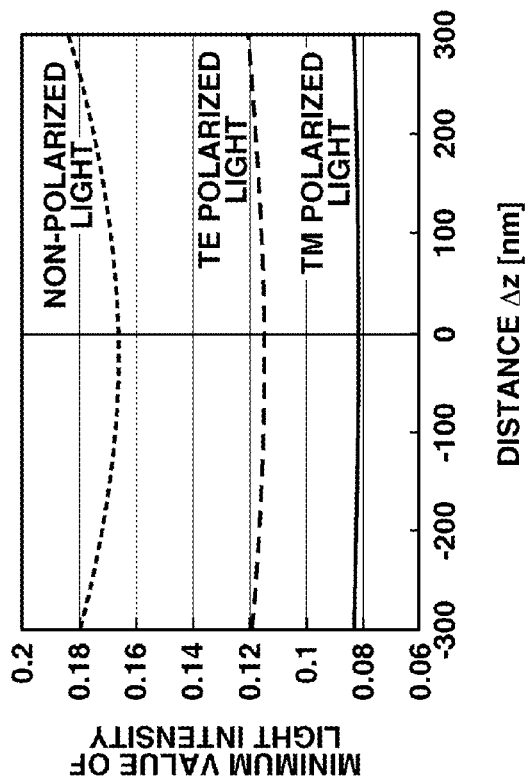
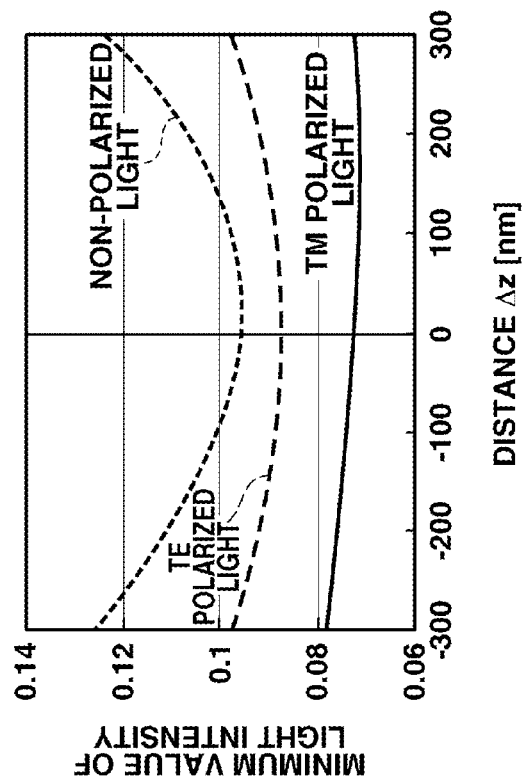
FIG.24A
FIG.24B

US 9,829,442 B2

DEFECT INSPECTING METHOD, SORTING METHOD AND PRODUCING METHOD FOR PHOTOMASK BLANK

CROSS-REFERENCE TO RELATED APPLICATION

This non-provisional application claims priority under 35 U.S.C. §119(a) on Patent Application No. 2015-174684 filed in Japan on Sep. 4, 2015, the entire contents of which are hereby incorporated by reference.

TECHNICAL FIELD

The present invention relates to a defect inspecting method for a photomask blank used for producing a photomask which, in turn, is used for manufacture of a semiconductor device or the like, particularly, to a technology effective for determination of the rugged shape (bump/pit shape) of a surface of a minute defect present in a thin film of a thickness of up to 10 nm formed in the photomask blank. Also, the invention relates to a photomask blank sorting method and a photomask blank producing method based on the application of the defect inspecting method for determination of the rugged shape of a defect in a photomask blank.

BACKGROUND ART

Semiconductor devices are manufactured by repeating a photolithographic technique in which exposure light is applied to a mask (transfer mask) such as a photomask with a circuit pattern drawn thereon and the circuit pattern formed on the mask is transferred onto a semiconductor substrate (semiconductor wafer) through a demagnification optical system. The transfer mask is produced by forming the circuit pattern in a substrate (mask blank) formed with an optical film. Such an optical film is generally a film composed mainly of a transition metal compound or a film composed mainly of a transition metal-containing silicon compound. As the optical film, a film functioning as a light-shielding film or a film functioning as a phase shift film is selected according to the purpose. Furthermore, a hard mask film may be formed as a processing aid film for the purpose of high-accuracy processing of an optical film.

The transfer mask such as photomask is for use as an original form for manufacturing semiconductor devices having minute patterns, and is demanded to be defect-free. This naturally leads to that the photomask blank is also demanded to be free of defects. In addition, at the time of forming a circuit pattern, a resist film for processing is formed on a photomask blank formed thereon with a film, and a final pattern is formed through ordinary lithography process such as an electron beam lithography. Therefore, the resist film is also demanded to be free of defects such as pinholes. Under such circumstances, many investigations have been made as to the defect detecting technique for photomasks and photomask blanks.

JP-A 2001-174415 (Patent Document 1) and JP-A 2002-333313 (Patent Document 2) describe a method of applying laser light to a substrate to detect a defect and/or a foreign matter from scattered light, particularly a technology in which asymmetry is imparted to detection signals to determine whether a defect in question is a bump defect or a pit defect. In addition, JP-A 2005-265736 (Patent Document 3) describes a technology in which deep ultraviolet (DUV) light conventionally used for general optical mask pattern inspection is used as inspection light. Further, JP-A 2013-19766 (Patent Document 4) describes a technology in which inspection light is used for scanning in the state of being divided into a plurality of spots and reflected beams are received by light detection elements. On the other hand, JP-A 2007-219130 (Patent Document 5) discloses a technology in which extreme ultraviolet (EUV) light having a wavelength of around 13.5 nm is used as inspection light to determine the rugged shape of a defect in an EUV mask blank.

CITATION LIST

Patent Document 1: JP-A 2001-174415
Patent Document 2: JP-A 2002-333313
Patent Document 3: JP-A 2005-265736
Patent Document 4: JP-A 2013-19766
Patent Document 5: JP-A 2007-219130

SUMMARY OF THE INVENTION

Attendant on the continued miniaturization of semiconductor devices, argon fluoride (ArF) lithography technique using ArF excimer laser light of a wavelength of 193 nm has been frequently used. In addition, a technology in which a process called multi-patterning consisting in combining an exposure process and a processing process multiple times is adopted to finally form a pattern with a sufficiently finer size as compared to the exposure wavelength has been vigorously investigated. As aforementioned, a transfer mask is used as an original form of fine patterns and, therefore, defects on the transfer mask that would hinder fidelity of pattern transfer must all be excluded. Accordingly, at the photomask blank production stage, also, those defects which obstruct mask pattern formation should all be detected.

In transfer masks, a pit defect, particularly a pinhole defect, is fatal to mask pattern formation. On the other hand, a bump defect may not necessarily be fatal to mask pattern formation, though it depends on the height of the defect. Therefore, exclusion of mask blanks having a defect while regarding all these bump defects as fatal defects leads to a lowering in the yield. Accordingly, in defect inspection, highly accurate discrimination of the rugged shapes of defects is very important for assured exclusion of mask blanks having a fatal defect and for securement of a good yield.

The inspection apparatuses described in Patent Documents 1 to 4 all adopt an optical defect detecting method. An optical defect detecting method is advantageous in that inspection of defects in a wide region can be performed in a comparatively short time and, by using a light source with a shorter wavelength, it becomes possible to accurately detect finer defects. In addition, the inspection apparatuses described in Patent Documents 1 to 4 provide a method in which whether a defect in question is a pit defect or a bump defect can be determined from the positional relation of a bright portion and a dark portion of detection signals obtained by an inspecting optical system using oblique illumination and/or a spatial filter. Further, Patent Document 5 describes a method for determination of the rugged shape of a phase defect, although the inspection object in this case is limited to EUV mask blank.

However, according to inspection experiments conducted using an atomic force microscope or an electron microscope jointly, it was found that there are cases where the rugged shape of a defect in a photomask blank cannot be determined by the method of examining the layout (positional relation)

of a bright portion and a dark portion of inspection signals concerning the photomask blank. Specifically, it was found that in regard of inspection signals concerning pit defects such as pinhole defects, the positional relation between a bright portion and a dark portion which is to be used for discrimination of the rugged shape may be unclear in some cases, and defects which are determined to be pit defects may include bump defects in some cases. Especially, a processing aid film such as a hard mask film to be used for advanced photomask processing may have a thickness of, for example, up to 10 nm, and it was found that the just-mentioned problem is liable to occur in determination of the rugged shape of a defect present in such a thin film.

The defect inspecting methods described in Patent Documents 1 to 4 do not necessarily make it possible to accurately determine the rugged shape of a defect. Besides, the defect inspecting method described in Patent Document 5 is a method which is applicable to phase defects intrinsic of EUV mask blanks but is not easily applicable to photomask blanks for use in ArF lithography which is the mainstream currently. Accordingly, there has been a demand for establishment of a technique by which the rugged shape of a defect present in a hard mask film reduced in thickness can be determined highly accurately, which has been difficult to achieve according to the conventional techniques.

Accordingly, an object of the present invention is to provide a defect inspecting method by which the rugged surface shape of a defect can be determined highly accurately while using an optical defect detecting method, particularly, a method for inspecting a defect present in a thin film of a thickness of up to 10 nm, such as a hard mask film used as a processing aid film in processing of a mask pattern, and a photomask blank sorting method and a photomask blank producing method based on the application of the defect inspecting method.

In order to fulfill the above need, the present inventors made investigations of a method for inspecting a defect present in a thin film of a thickness of up to 10 nm such as a hard mask film formed on an optical film, through actual measurements by an optical detecting method and through simulations. As a result of their investigations, the present inventors found out that variations in brightness/darkness of light intensity of an observed image based on the optical detecting method and the positional relation of bright and dark portions of light intensity are different for different modes of defects, depending on the values of reflectance and complex refractive index of the optical film and the thin film formed thereon with respect to inspection light, and the like.

Then, as a result of their further investigations, the present inventors found out that when an inspection treatment procedure and a criterion for determination of the rugged shape of a defect are determined according to the mode of the optical film and the thin film and the mode of defects, inspection images of the defects are collected by an optical detecting method according to the inspection treatment procedure and the criterion for determination, and the light intensity distribution (light intensity profile) of the inspection images, particularly the layout (positional relation) of bright and dark portions and the light intensity or intensity difference of the bright and dark portions, are evaluated, then it is possible to distinguish a pit defect and a bump defect from each other more accurately. Based on the findings, the present inventors have come to make the present invention.

In one aspect of the present invention, there is provided a method of inspecting a defect present at a surface portion of a photomask blank by use of an inspecting optical system, the photomask blank including an optical film formed on a substrate, and a thin film formed in contact with a side of the optical film opposite to the substrate, the thin film being formed as an outermost surface layer.

The defect inspecting method includes:

(A1) a step of preparing the photomask blank;

(A2) a step of selecting and designating an inspection treatment procedure and a criterion for determination of rugged shape of the defect which correspond to mode of the optical film and the thin film of the photomask blank;

(A3) a step of moving the photomask blank to move the defect into an observation position of the inspecting optical system, applying inspection light to a region including the defect while maintaining a distance between the defect and an objective lens of the inspecting optical system, based on the inspection treatment procedure designated in the step (A2), and collecting reflected light from the region irradiated with the inspection light, as a magnified image of the region, through the inspecting optical system; and (A4) a step of determining the rugged shape of the defect, from light intensity distribution of the magnified image, based on the criterion for determination designated in the step (A2).

In the defect inspecting method, preferably, the step (A4) includes: a treatment of comparing variation in light intensity level of a defect portion of the magnified image with light intensity level of a portion surrounding the defect; and a treatment of comparing the result of the comparing treatment with the criterion for determination.

In the defect inspecting method, preferably, the distance in the step (A3) is a focus distance, and an inspection light application condition in the step (A3) is that the inspection light is non-polarized light.

In the defect inspecting method, preferably, the inspection treatment procedure of the step (A2) includes a plurality of inspection conditions concerning the step (A3), and the step (A4) is conducted after the step (A3) is performed sequentially for all the inspection conditions included in the inspection treatment procedure.

In the defect inspecting method, preferably, the plurality of inspection conditions include an inspection condition where the distance in the step (A3) is a focus distance and an inspection condition where the distance in the step (A3) is a defocus distance.

In the defect inspecting method, preferably, the plurality of inspection conditions include an inspection condition where the distance in the step (A3) is a focus distance, an inspection condition where the distance in the step (A3) is a positive defocus distance, and an inspection condition where the distance in the step (A3) is a negative defocus distance.

In the defect inspecting method, preferably, the plurality of inspection conditions include an inspection condition where an inspection light application condition in the step (A3) is that the inspection light is non-polarized light, and an inspection condition where an inspection light application condition in the step (A3) is that the inspection light is polarized light.

In the defect inspecting method, preferably, the plurality of inspection conditions include an inspection condition where an inspection light application condition in the step (A3) is that the inspection light is non-polarized light, an inspection condition where an inspection light application condition in the step (A3) is that the inspection light is transverse electric (TE) polarized light, and an inspection condition where an inspection light application condition in the step (A3) is that the inspection light is transverse magnetic (TM) polarized light.

In the defect inspecting method, preferably, the plurality of inspection conditions include an inspection condition where the distance and an inspection light application condition in the step (A3) are a positive defocus distance and that the inspection light is TE polarized light, an inspection condition where the distance and an inspection light application condition in the step (A3) are a positive defocus distance and that the inspection light is TM polarized light, an inspection condition where the distance and an inspection light application condition in the step (A3) are a negative defocus distance and that the inspection light is TE polarized light, and an inspection condition where the distance and an inspection light application condition in the step (A3) are a negative defocus distance and that the inspection light is TM polarized light, and wherein collection of a magnified image is conducted under each of the inspection conditions.

In the defect inspecting method, preferably, the plurality of inspection conditions further include an inspection condition where the distance and an inspection light application condition in the step (A3) are a focus distance and that the inspection light is TE polarized light, and an inspection condition where the distance and an inspection light application condition in the step (A3) are a focus distance and that the inspection light is TM polarized light.

In the defect inspecting method, preferably, the step (A4) includes a treatment of calculating a minimum value of light intensity level of a defect portion of each magnified image, and a treatment of comparing the result of the calculating treatment with the criterion for determination.

In the defect inspecting method, preferably, the thin film is a hard mask film.

In the defect inspecting method, preferably, the thin film has a thickness of up to 10 nm.

In the defect inspecting method, preferably, the inspection light is light having a wavelength of 210 to 550 nm.

In the defect inspecting method, preferably, the inspection light is applied by oblique illumination in which optical axis of the inspection light is inclined at a predetermined angle in relation to a normal to that surface of the thin film which is irradiated with the inspection light.

In the defect inspecting method, preferably, in the step (A3), the photomask blank is placed on a stage which can be moved in an in-plane direction of the photomask blank, and the stage is moved in the in-plane direction to bring the defect and an objective lens of the inspecting optical system close to each other.

In another aspect of the present invention, there is provided a method of sorting a photomask blank, including sorting out a photomask having no pit defect, based on rugged shapes of defects determined by the above-mentioned defect inspecting method.

In a further aspect of the present invention, there is provided a method of producing a photomask blank, including:

a step of forming an optical thin film on a substrate and forming a thin film, as an outermost surface layer, on a side of the optical film opposite to the substrate; and a step of determining rugged shape of a defect present in the thin film by the above-mentioned defect inspecting method.

Advantageous Effects of the Invention

According to the described aspects of the present invention, defects in photomask blanks can be inspected with highly reliable discrimination of the rugged shapes of the defects, while using an optical defect inspecting method. In addition, by application of the defect inspecting method disclosed herein, it is possible to reliably exclude photomask blanks having a pit defect that is a fatal defect, and to provide photomask blanks having no fatal defect at a lower cost and in a high yield.

BRIEF DESCRIPTION OF THE DRAWINGS

FIGS. 1A and 1B are sectional views for illustrating an example of the presence of a defect in a photomask blank, wherein FIG. 1A shows a photomask blank in which a pit defect is present, and FIG. 1B shows a photomask produced from the photomask blank in which the pit defect is present.

FIG. 4A is a conceptual diagram showing a mode of regular reflected light in relation to inspection light applied by oblique illumination toward a typical pit defect on a photomask blank, and FIG. 4B is a diagram showing a sectional profile of light intensity distribution of an inspection image.

FIG. 7 is a diagram showing film thickness dependency of inspection light reflectance of the hard mask film of the photomask blank illustrated in FIGS. 6A and 6B.

FIG. 18A is a sectional view of a photomask blank having a pit defect formed in a hard mask film and an optical film in Example 1, and FIG. 18B is a diagram showing a sectional profile of light intensity distribution of an inspection image obtained at a focus distance.

FIGS. 24A and 24B are diagrams showing distance dependency of a minimum value in light intensity distribution of inspection images of defects in the photomask blank shown in FIGS. 23A and 23B.

DESCRIPTION OF THE PREFERRED EMBODIMENTS

Figure 2:
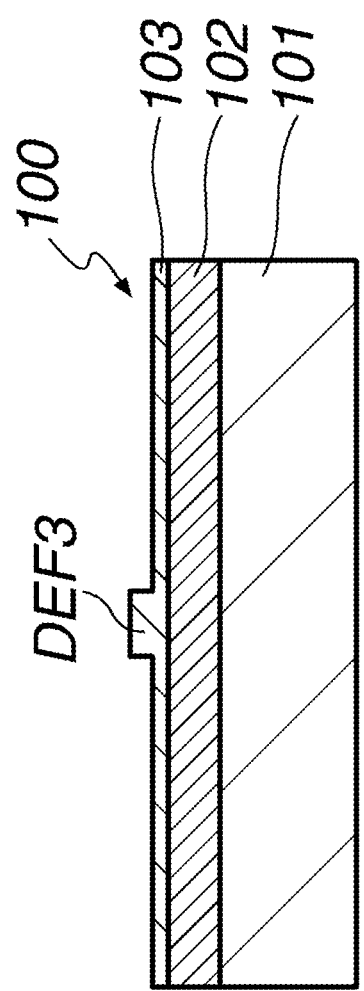
FIG. 2 is a sectional view for illustrating another example of the presence of a defect in a photomask blank, showing a photomask blank on which a bump defect is present.

If a defect such as a pinhole is present in a thin film of a photomask blank, it causes a defect in a mask pattern on a photomask that is produced by use of the photomask blank. A typical example of a pit defect in a photomask blank is illustrated in FIGS. 1A and 1B. FIG. 1A is a sectional view showing a photomask blank 100 wherein an optical film 102 functioning as a light-shielding film, a phase shift film such as a halftone phase shift film or the like and a hard mask film (processing aid film) 103 for performing highly accurate processing of the optical film 102 are formed over a transparent substrate 101. In this case, a pinhole defect DEF1 is present in the hard mask film 103. If a photomask is produced by an ordinary production process from such a photomask blank 100 as just illustrated, a pinhole defect would be formed in the optical film 102 at a position corresponding to the pinhole defect DEF1 in the hard mask film 103. Consequently, a photomask is produced in which a defect DEF2 arising from the photomask blank is present in an optical film pattern 102a, such as a photomask 100a depicted in FIG. 1B. Such a defect as this brings about a pattern transfer error in exposure conducted using the photomask. Therefore, it is necessary to detect a defect in a photomask blank at a stage before processing of the photomask blank, and to exclude the photomask blank accompanied by the defect or to correct the defect.

On the other hand, FIG. 2 illustrates an example of a bump defect present on a photomask blank. Specifically, FIG. 2 is a sectional view illustrating an example of a photomask blank 100 in which an optical film 102 and a hard mask film 103 are formed over a transparent substrate 101, and a bump defect DEF3 formed as one body with the hard mask film 103 is present on the hard mask film 103. In the case of such a photomask blank 100 as this, a pinhole defect DEF2 in the optical film 102 like that in the case shown in FIG. 1B is not formed. Therefore, such a bump defect ordinarily does not constitute a fatal defect. In addition, a bump defect due to a foreign matter adhered to a surface of a photomask blank does not become a fatal defect if it can be removed by cleaning.

In this way, determination of whether a defect present on a photomask blank is a pit defect such as a pinhole that is a fatal defect or is a bump defect that is not necessarily a fatal defect will be an important factor concerning the guarantee of photomask blank quality and the yield in photomask blank production. In view of this, it is desirable to establish a method by which rugged shapes (bump/pit shapes) of defects can be discriminated with high reliability while using an optical inspection technique.

Figure 3:
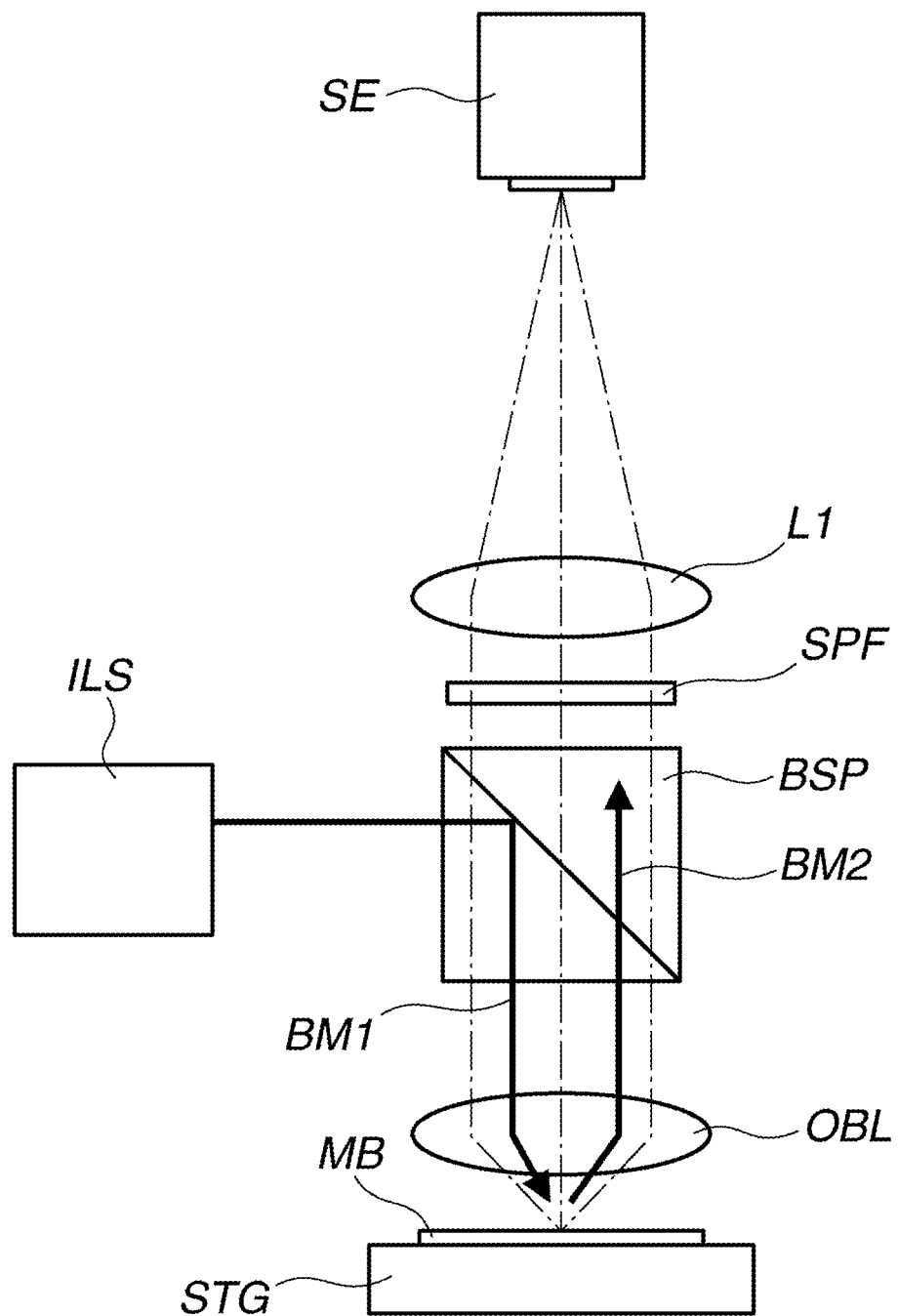
FIG. 3 illustrates an example of configuration of an inspecting optical system for use in defect inspection of a photomask blank.

In the first place, an inspecting optical system preferably used for defect inspection of a photomask blank, specifically, an inspecting optical system preferably used for determining the rugged shape of a defect at a surface portion of a photomask blank will be described. FIG. 3 is a conceptual diagram showing an example of basic configuration of an inspecting optical system, which includes a light source ILS, a beam splitter BSP, an objective lens OBL, a stage STG which can be moved with a photomask blank MB mounted thereon, and an image detector SE. The light source ILS is configured to be able to emit light of a wavelength of approximately 210 to 550 nm, and inspection light BM1 emitted from the light source ILS is deflected by the beam splitter BSP, to be applied to a predetermined region of the photomask blank MB through the objective lens OBL. Reflected light BM2 from a surface of the photomask blank MB is collected by the objective lens OBL, and passes through the beam splitter BSP and a lens L1 to reach a light receiving surface of the image detector SE. In this case, the position of the image detector SE is controlled in such a manner that a magnified inspection image of the surface of the photomask blank MB is formed on the light receiving surface of the image detector SE. Then, data of the magnified inspection image collected at the image detector SE is subjected to image processing calculation, whereby calculation of defect size and determination of the rugged shape of the defect are conducted, and the results are recorded as defect information.

The magnified inspection image can be collected, for example, by a direct method in which a detector having a multiplicity of optical detection elements arrayed as pixels such as a charge-coupled device (CCD) camera is used as the image detector SE, and a magnified image formed by the reflected light BM2 from the surface of the photomask blank MB through the objective lens OBL is collected as a two-dimensional image. Alternatively, a method may be adopted in which the surface of the photomask blank MB is scanned with the inspection light BM1 by scanning means, light intensity of the reflected light BM2 is sequentially collected by the image detector SE, the collected signals are recorded through photoelectric conversion, and a two-dimensional image of the whole area of the photomask blank MB is produced. Further, a spatial filter SPF for shielding part of the reflected light BM2 may be disposed at a pupil position of the inspecting optical system, for example, on an optical path of the reflected light BM2, particularly between the beam splitter BSP and the lens L1. In this case, part of the optical path of the reflected light BM2 may be shielded as required, whereby a magnified inspection image can be captured by the image detector SE. The incidence angle of the inspection light BM1 can be set to a predetermined angle in relation to the photomask blank MB. Note that positioning of the defect to be inspected may be conducted in such a manner that the defect as an inspection object can be observed through the objective lens OBL. In this case, the photomask blank MB is placed on the mask stage STG, and the photomask blank MB can be positioned such as to be observable through the objective lens OBL, by movement of the mask stage STG. Note that polarized-light illumination can be adopted by inserting a polarizing plate, if required, into a predetermined position in the optical path, though not illustrated.

In the next, referring to FIGS. 4A, 4B, 5A and 5B, description will be made of a difference between an inspection image of a pit defect and an inspection image of a bump defect in the case where the distance between a defect and the objective lens of the inspecting optical system is set to a focusing distance (herein referred to as focus distance) and reflected light is collected in this condition. FIG. 4A is a conceptual diagram showing an example in which inspection light BM1 from the inspecting optical system shown in FIG. 3 is applied to a surface MBS of a photomask blank having a typical pit defect DEF4 obliquely from a left side. Such oblique illumination can be realized, for example, by a method wherein the position of the inspection light BM1 applied to the photomask blank MB from the light source ILS shown in FIG. 3 is controlled by controlling the position of aperture (located between the light source ILS and the beam splitter BSP). In this case, the reflected light BM2 reflected on a side surface LSF on the left side of the pit defect DF4 in the figure is concentrated on the right side relative to the objective lens OBL by regular reflection and, hence, is not sufficiently taken into the objective lens OBL. On the other hand, the reflected light reflected on a side surface RSF on the right side of the pit defect DEF4 in the figure is sufficiently taken into the objective lens OBL through regular reflection. As a result, the light intensity distribution of an inspection image obtained at the image detector assumes a sectional profile PR1 as shown in FIG. 4B, wherein the left side of the pit defect DEF4 is a dark portion and the right side is a bright portion.

Figures 5A, 5B:
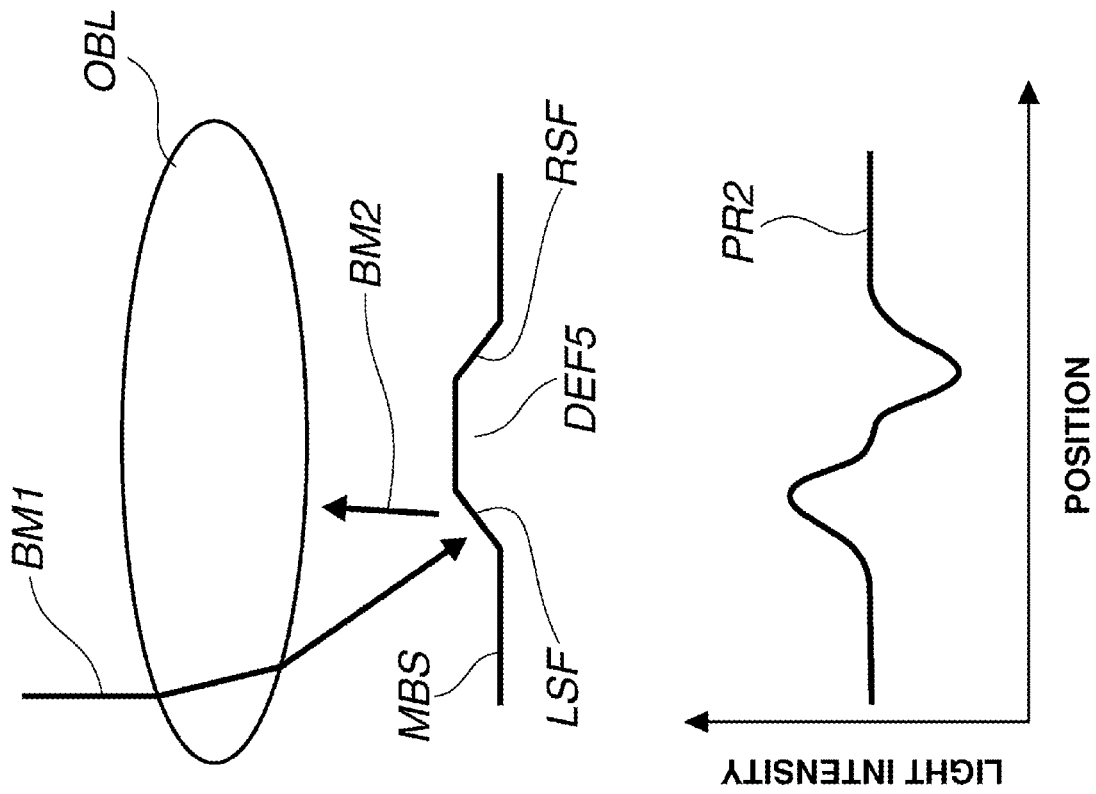
FIG. 5A is a conceptual diagram showing a mode of regular reflected light in relation to inspection light applied by oblique illumination toward a typical bump defect on a photomask blank.
FIG. 5B is a diagram showing a sectional profile of light intensity distribution of an inspection image.

On the other hand, FIG. 5A is a conceptual diagram showing an example in which inspection light BM1 from the inspecting optical system shown in FIG. 3 is applied to a surface MBS of a photomask blank having a typical bump defect DEF5 obliquely from a left side. In this case, the reflected light BM2 reflected on a side surface LSF on the left side of the bump defect DEF5 in the figure is sufficiently taken into the objective lens OBL through regular reflection. On the other hand, the reflected light reflected on a side surface RSF on the right side of the bump defect DEF5 in the figure is concentrated on the right side relative to the objective lens OBL by regular reflection and, hence, is not sufficiently taken into the objective lens OBL. As a result, the light intensity distribution of the inspection image obtained at the image detector SE assumes a sectional profile PR2 as shown in FIG. 5B, wherein the left side of the bump defect DEF5 is a bright portion and the right side is a dark portion.

In addition, in the case where a spatial filter SPF for shielding part of reflected light is provided on an optical path of the reflected light in the inspecting optical system and the reflected light is collected through the spatial filter SPF, as illustrated in FIG. 3, it is ensured that even when a surface of a photomask blank is illuminated with normal incident inspection light, bright and dark portions can be generated in the inspection image, like in the case where the aforementioned oblique illumination is used. In this case, if for example one half of beam in the optical path of the reflected light is shielded, the rugged shape of a defect can be determined from the positional relation between bright and dark portions of the inspection image or from the difference in light intensity between the bright and dark portions, while taking the inspection light incidence side as a reference.

In this way, by application of oblique illumination, the rugged shape of a defect which is a typical pit defect or bump defect can be determined from the positional relation of bright and dark portions of the inspection image obtained. While an example of oblique illumination from a left side in the drawing has been shown in FIGS. 4A, 4B, 5A and 5B, the illumination direction can be set arbitrarily, and by taking the inspection light incidence side as a reference in the inspection image obtained, the rugged shape of a defect can be similarly determined from the positional relation between bright and dark portions of the inspection image or from the difference in light intensity between the bright and dark portions.

According to film mode of a photomask blank, however, there are cases where whether a defect is a pit defect or a bump defect cannot be accurately determined based only on the aforementioned positional relation between bright and dark portions of the inspection image. Examples of such cases will be described below.

First Film Mode

First, description will be made of light intensity distribution of an inspection image in a case where a film of a high reflectance (in an example described later, a hard mask film 103 corresponds to this film) as an outermost surface layer apart from a transparent substrate, and a film (in the example described later, an optical film 102 corresponds to this film) having a reflectance equal to or lower than that of the high-reflectance film and being in contact with a side of the high-reflectance film opposite to the transparent substrate are formed over the transparent substrate, and where the high-reflectance film is small in thickness.

Figure 6A:
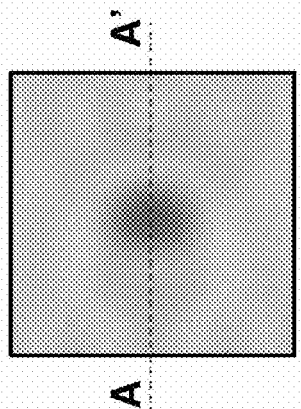
FIG. 6A is a plan view of a photomask blank having a pit defect in a hard mask film in a first film mode.
Figure 6B:
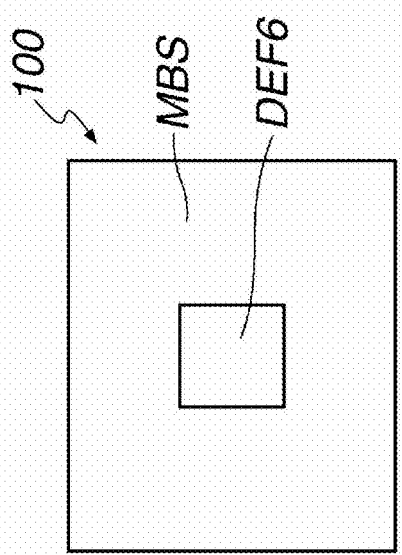
FIG. 6B is a sectional view of the same.
Figure 6C:
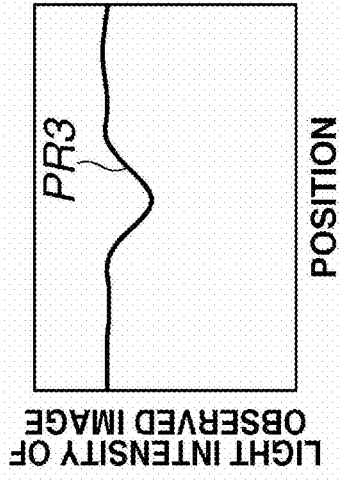
FIG. 6C is an inspection image of the pit defect.
Figure 6D:
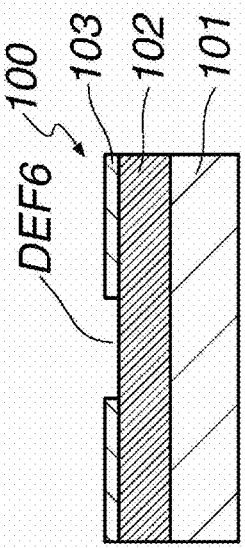
FIG. 6D is a diagram showing a sectional profile of light intensity distribution of an inspection image.

FIGS. 6A and 6B are a plan view and a sectional view of a photomask blank 100 having a pit defect. These figures illustrate a state in which an optical film 102 formed from a molybdenum silicide (MoSi) material and a hard mask film 103 formed from a chromium (Cr) material in a thickness of approximately 10 nm are formed over a transparent substrate 101 such as quartz substrate transparent to inspection light, and a pit defect DEF6 such as a pinhole defect is present in the hard mask film 103. In the case where the inspecting optical system shown in FIG. 3 is used with the distance between the pit defect DEF6 and the objective lens of the inspecting optical system set to a focus distance, inspection light is applied to a surface MBS of the photomask blank from a left side in FIGS. 6A and 6B by oblique illumination and where reflected light is collected, an inspection image having a light intensity distribution shown in FIG. 6C is obtained. In addition, light intensity distribution in a section along line A-A' of FIG. 6C assumes a sectional profile PR3 as shown in FIG. 6D. In this case, the light intensity distribution of the inspection image includes only a dark portion, without any bright portion appearing at the part of the pit defect DEF6, and, hence, does not correspond to the light intensity distribution of the inspection image of a typical pit defect depicted in FIGS. 4A and 4B.

The reason why the pit defect in this case is observed as being composed only of a dark portion is considered to reside in that since the pit defect DEF6 is not large in depth, the quantity of reflected light from a side surface of the defect is small, and the influence of inspection light reflectance on variations in light intensity is rather greater. FIG. 7 is a diagram showing the relation between the thickness of the hard mask film 103 formed from a Cr material on the optical film 102 formed from an MoSi material of the photomask blank 100 depicted in FIGS. 6A and 6B and inspection light reflectance. In FIG. 7, the reflectance at the zero thickness corresponds to the reflectance (in the drawing, REF10) at the pit defect portion of the hard mask film 103, and this reflection is reflection from the optical film 102. On the other hand, the reflectance at a predetermined thickness of the hard mask film 103 (in the drawing, TH1) corresponds to the reflectance (in the drawing, REF11) at a non-defect portion (for example, a portion surrounding the defect) of the hard mask film 103, and this reflection is reflection from the hard mask film 103. In this case, REF10 is lower than REF11 (REF10<REF11), and this is considered to be the reason why the pit defect portion is observed as a dark portion as a whole. Thus, in the case where a pit defect is formed only in the hard mask film 103, the light intensity distribution of the defect portion of the observed image is not the typical pit defect light intensity distribution in which the left side is a dark portion and the right side is a bright portion as shown in FIGS. 4A and 4B.

However, in the case where the pit defect is sufficiently deep, for example, where the pit defect penetrates the hard mask film 103 and is formed further in the optical film 102 also, the quantity of reflected light from a side surface of the defect is correspondingly large, and a sufficient difference is generated between the quantity of reflected light from the left side surface and the quantity of reflected light from the right side surface. Consequently, an observed image is obtained in which the left side is a dark portion and the right side is a bright portion, corresponding to the light intensity distribution of the inspection image of the typical pit defect shown in FIGS. 4A and 4B.

Figure 8A:
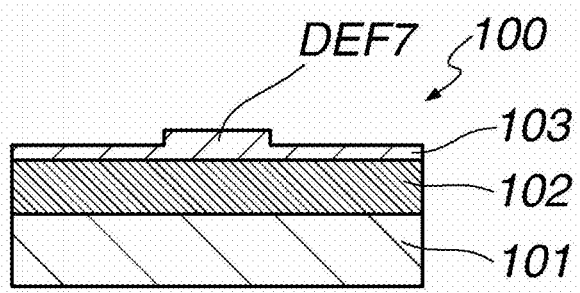
FIG. 8A is a sectional view of a photomask film having a bump defect on a hard mask film in a first film mode.
Figure 8B:
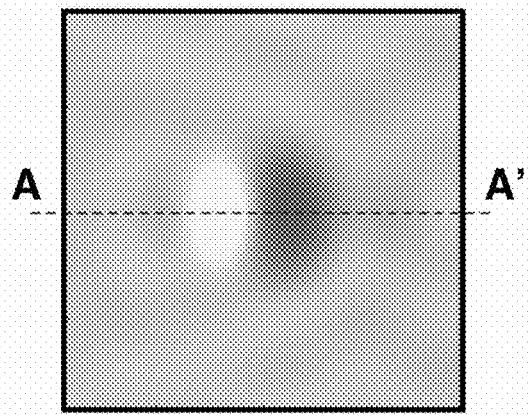
FIG. 8B is an inspection image of the bump defect.
Figure 8C:
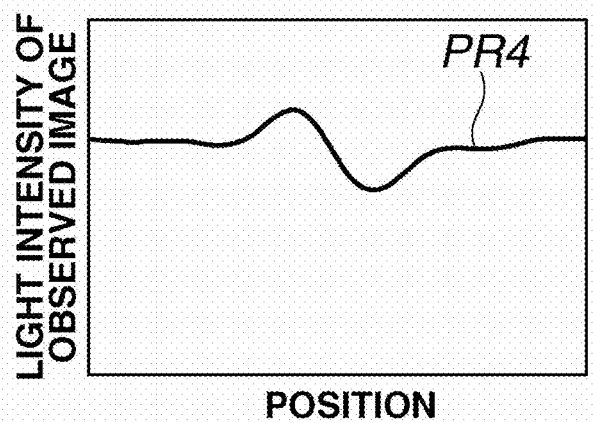
FIG. 8C is a diagram showing a sectional profile of light intensity distribution of the inspection image.

On the other hand, FIG. 8A is a sectional view of a photomask blank 100 having a bump defect. This figure illustrates a state in which an optical film 102 formed from an MoSi material and a hard mask film 103 formed from a Cr material in a thickness of approximately 10 nm are formed over a transparent substrate 101 such as quartz substrate transparent to inspection light, and a bump defect DEF7 formed from the same material (e.g., Cr material) as that of the hard mask film 103 is present on the hard mask film 103. In the case where the inspecting optical system illustrated in FIG. 3 is used with the distance between the bump defect DEF7 and the objective lens of the inspecting optical system set to a focus distance, inspection light is applied to a surface of the photomask blank from a left side in FIG. 8A by oblique illumination and where reflected light is collected, an inspection image having a light intensity distribution depicted in FIG. 8B is obtained. In addition, the light intensity distribution in a section along line A-A' of FIG. 8B assumes a sectional profile PR4 shown in FIG. 8C. In this case, the light intensity distribution of the inspection image, specifically at the part of the bump defect DEF7, has a bright portion on the left side and a dark portion on the right side, in the same manner as the light intensity distribution in the case of the typical bump defect illustrated in FIGS. 5A and 5B.

From the above, the rugged shape of a defect in the first film mode can be determined as follows:

(1-1) if a defect portion in the light intensity distribution of the observed image has only a dark portion, the defect is a pit defect formed only in the high-reflectance film (hard mask film 103);

(1-2) if a defect portion in the light intensity distribution of the observed image has a dark portion on the left side and a bright portion on the right side, the defect is a pit defect which penetrates the high-reflectance film (hard mask film 103) and is further formed also in the film (optical film 102) having a reflectance equal to or lower than that of the high-reflectance film; and (1-3) if a defect portion in the light intensity distribution of the observed image has a bright portion on the left side and a dark portion on the right side, the defect is a bump defect.

The criterion for determination in the first film mode is different from the criterion in the cases of the typical pit defect and bump defect illustrated in FIGS. 4A, 4B, 5A and 5B, but is peculiar to the case of the first film mode. The criterion for determination in the first film mode is preferable for use in the case where a high-reflectance film as an outermost surface layer apart from a transparent substrate and a film having a reflectance equal to or lower than that of the high-reflectance film and being in contact with a side of the high-reflectance film opposite to the transparent substrate are formed over the transparent substrate and where the high-reflectance film has a small thickness, for example, a thickness of 5 to 10 nm.

Second Film Mode

In the next, description will be made of light intensity distribution of an inspection image in a case where a film formed from a material substantially transparent to inspection light (in an example described later, a hard mask film 103 corresponds to this film) as an outermost surface layer apart from a transparent substrate, and a film (in the example described later, an optical film 202 corresponds to this film) being opaque or semi-transparent to the inspection light and being in contact with the transparent substrate side of the film of the material substantially transparent to the inspection light are formed over the transparent substrate, and where the film of the material substantially transparent to the inspection light is small in thickness.

Figure 9A:
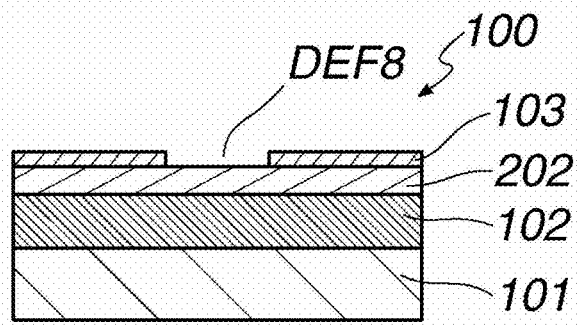
FIG. 9A is a sectional view of a photomask blank having a pit defect in a hard mask film in a second film mode.
Figure 9B:
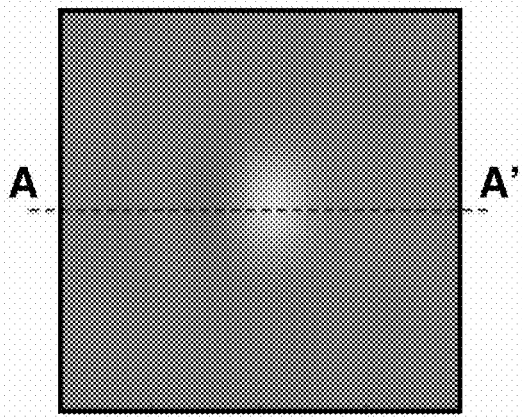
FIG. 9B is an inspection image of the pit defect.
Figure 9C:
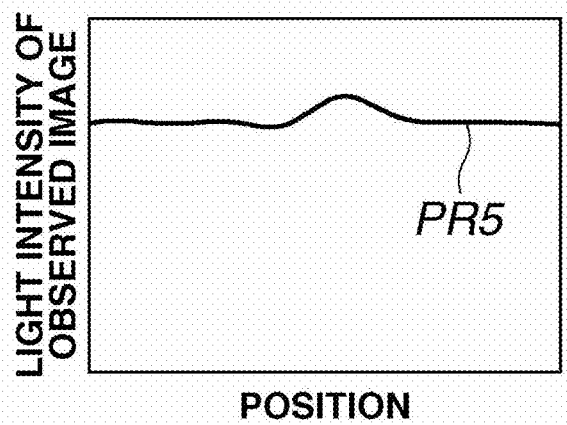
FIG. 9C is a diagram showing a sectional profile of light intensity distribution of the inspection image.

FIG. 9A is a sectional view of a photomask blank 100 having a pit defect. This figure illustrates a state in which an optical film 102 formed from an MoSi material, an optical film 202 formed from, a Cr material, and a hard mask film 103 formed from a material substantially transparent to the inspection light, for example, silicon oxide or the like and having a thickness of approximately 5 to 10 nm are formed over a transparent substrate 101 such as quartz substrate transparent to the inspection light, and in which a pit defect DEF8 such as a pinhole defect is present in the hard mask film 103. In the case where the inspecting optical system shown in FIG. 3 is used with the distance between the pit defect DEF8 and the objective lens of the inspecting optical system set to a focus distance, inspection light is applied to a surface of the photomask blank from a left side in FIG. 9A by oblique illumination and where reflected light is collected, an inspection image having a light intensity distribution as shown in FIG. 9B is obtained. In addition, the light intensity distribution in a section along line A-A' of FIG. 9B assumes a sectional profile PR5 as depicted in FIG. 9C. In this case, the light intensity distribution of the inspection image, specifically at the part of the pit defect DEF8, is predominantly a bright portion, although it is slightly dark on the left side, and substantially has only a bright portion. Thus, a clear difference between bright and dark portions as seen in the light intensity distribution of the inspection image of the typical pit defect shown in FIGS. 4A and 4B does not appear in this case.

Figure 10:
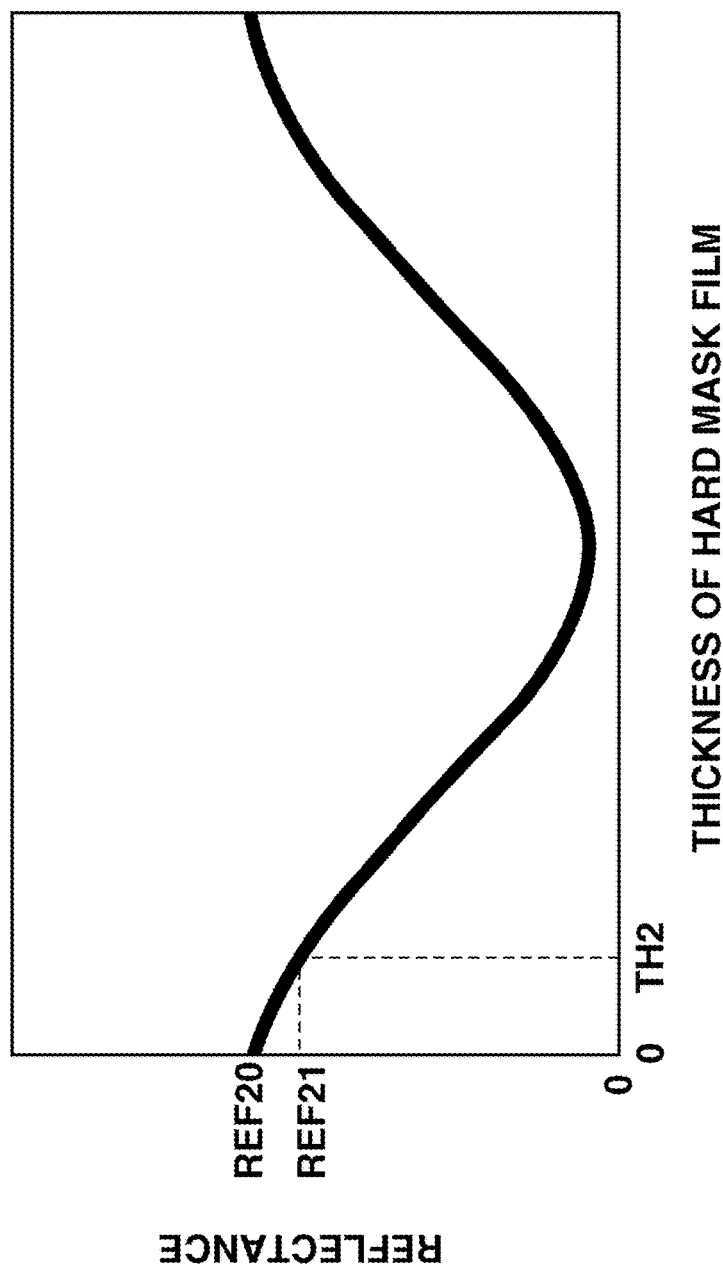
FIG. 10 is a diagram showing film thickness dependency of inspection light reflectance of the hard mask film of the photomask blank shown in FIG. 9A.

The reason why the bright portion is observed predominantly with respect to the pit defect in this case is considered to reside in that since the pit defect DEF8 is not large in depth, the quantity of reflected light from a side surface of the defect is small, and the influence of inspection light reflectance on variations in light intensity is rather greater, like in the case of the pit defect DEF6 in the first film mode illustrated in FIGS. 6A to 6D. FIG. 10 is a diagram showing the relation between the thickness of the hard mask film 103, formed from a material substantially transparent to inspection light and formed on the optical film 202 formed from a Cr material, of the photomask blank 100 depicted in FIG. 9A and inspection light reflectance. In FIG. 10, the reflectance at the zero thickness corresponds to the reflectance (in the drawing, REF20) at the pit defect portion of the hard mask film 103, and this reflection is reflection from the optical film 202. On the other hand, the reflectance at a predetermined thickness of the hard mask film 103 (in the drawing, TH2) corresponds to the reflectance (in the drawing, REF21) at a non-defect portion (for example, a portion surrounding the defect) of the hard mask film 103, and this reflection is reflection from the hard mask film 103. In this case, REF20 is higher than REF21 (REF20>REF21), and this is considered to be the reason why the bright portion is observed predominantly in regard of the defect portion. Thus, in the case where a pit defect is formed only in the hard mask film 103, the light intensity distribution of the defect portion of the observed image is not the typical pit defect light intensity distribution in which the left side is a dark portion and the right side is a bright portion as shown in FIGS. 4A and 4B.

However, in the case where the pit defect is sufficiently deep, for example, where the pit defect penetrates the hard mask film 103 and is further formed also in the optical film 202, the quantity of reflected light from a side surface of the defect is correspondingly large, and a sufficient difference is generated between the quantity of reflected light from the left side surface and the quantity of reflected light from the right side surface. Consequently, an observed image is obtained in which the left side is a dark portion and the right side is a bright portion, corresponding to the light intensity distribution of the inspection image of the typical pit defect shown in FIGS. 4A and 4B.

Figure 11A:
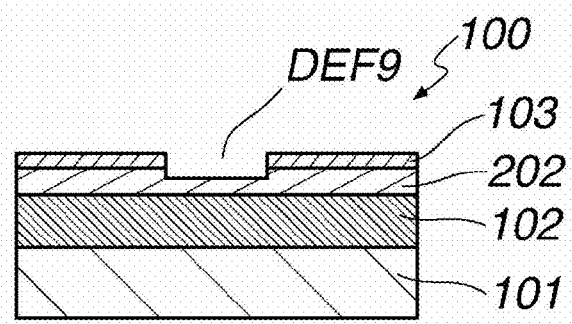
FIG. 11A is a sectional view of a photomask blank having a pit defect in a hard mask film and an optical film in a second film mode.
Figure 11B:
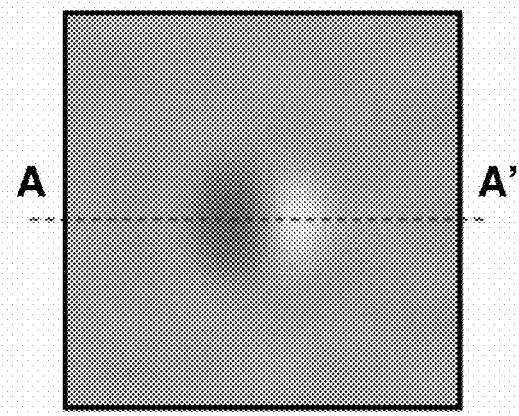
FIG. 11B is an inspection image of the pit defect.
Figure 11C:
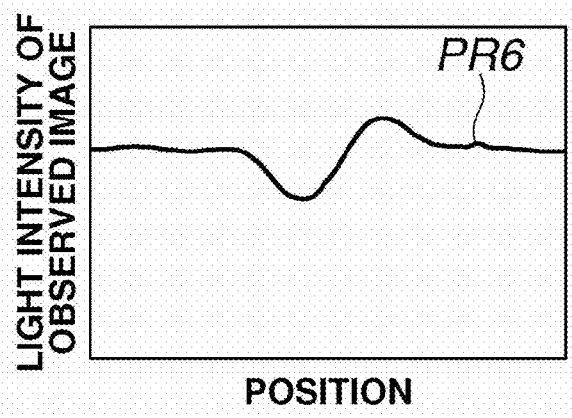
FIG. 11C is a diagram showing a sectional profile of light intensity distribution of the inspection image.

FIG. 11A is a sectional view of a photomask blank 100 having a pit defect. This figure illustrates a state in which an optical film 102 formed from an MoSi material, an optical film 202 formed from a Cr material, and a hard mask film 103 formed from a material substantially transparent to inspection light, for example, silicon oxide or the like and having a thickness of approximately 5 to 10 nm are formed over a transparent substrate 101 such as quartz substrate transparent to the inspection light, and in which a pit defect DEF9 such as a pinhole defect penetrates the hard mask film 103 and is further formed also in the optical film 202. In the case where the inspecting optical system shown in FIG. 3 is used with the distance between the pit defect DEF9 and the objective lens of the inspecting optical system set to a focus distance, inspection light is applied to a surface of the photomask blank from a left side in FIG. 11A by oblique illumination and where reflected light is collected, an inspection image having a light intensity distribution as shown in FIG. 11B is obtained. In addition, the light intensity distribution in a section along line A-A' of FIG. 11B assumes a sectional profile PR6 as depicted in FIG. 11C. In this case, the light intensity distribution of the inspection image, specifically at the part of the pit defect DEF9, has a dark portion on the left side and a bright portion on the right side, and, hence, shows a similar light intensity distribution to that in the case of the typical pit defect shown in FIGS. 4A and 4B.

Figure 12A:
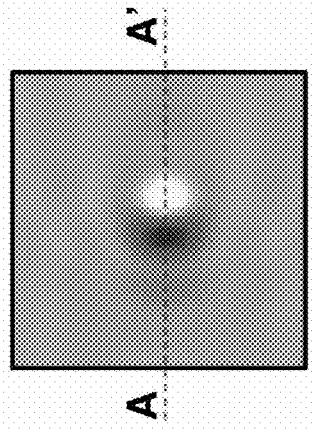
FIG. 12A is a plan view of a photomask blank having a bump defect on a hard mask film in a second film mode.
Figure 12B:
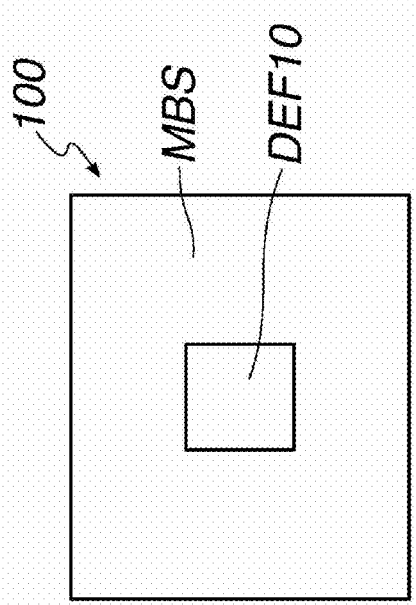
FIG. 12B is a sectional view of the same.
Figure 12C:
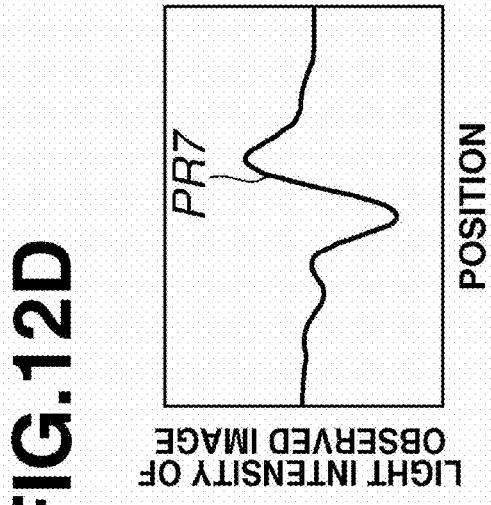
FIG. 12C is an inspection image of the bump defect.
Figure 12D:
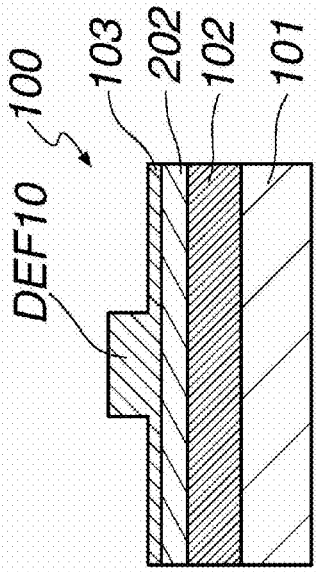
FIG. 12D is a diagram showing a sectional profile of light intensity distribution of the inspection image.

FIGS. 12A and 12B are a plan view and a sectional view of a photomask blank 100 having a bump defect. These figures illustrate a state in which an optical film 102 formed from an MoSi material, an optical film formed from a Cr material and a hard mask film 103 formed from a material substantially transparent to inspection light, such as silicon oxide or the like, and having a thickness of approximately 5 to 10 nm are formed over a transparent substrate 101 such as quartz substrate transparent to the inspection light, and in which a bump defect DEF10 formed from the same material as that of the hard mask film 103 (for example, a material substantially transparent to the inspection light) is present on the hard mask film 103. In the case where the inspecting optical system shown in FIG. 3 is used with the distance between the bump defect DEF10 and the objective lens of the inspecting optical system set to a focus distance, inspection light is applied to a surface MBS of the photomask blank from a left side in FIGS. 12A and 12B by oblique illumination and where reflected light is collected, an inspection image having a light intensity distribution as shown in FIG. 12C is obtained. In addition, light intensity distribution in a section along line A-A' of FIG. 12C assumes a sectional profile PR7 as shown in FIG. 12D. In this case, the light intensity distribution of the inspection image, specifically at the part of the bump defect DEF10, has a dark portion on the left side and a bright portion on the right side.

Especially, more clear dark and bright portions appear in the case of a bump defect having a height of more than 50 nm.

In this way, in the case where a thin film such as a hard mask film is formed with a bump defect composed of the same material as that of the thin film, the light intensity distribution of the defect portion of the observed image is not like that of a typical bump defect in which the left side is a bright portion and the right side is a dark portion as depicted in FIGS. 5A and 5B. In this case, moreover, the same positional relation between bright and dark portions of the inspection image as that in the case where the pit defect penetrates the hard mark film 103 and is further formed also in the optical film 202 as depicted in FIGS. 11A to 11C is shown, and, accordingly, both of the bump defect shown in FIGS. 12A and 12B and the pit defect shown in FIG. 11A cannot be discriminated from each other on the basis of the positional relation between the bright and dark portions of the inspection image.

However, in regard of such a pit defect as shown in FIG. 11A and such a bump defect as shown in FIGS. 12A and 12B, the following has been found. In the case where the distance between the defect and the objective lens of the inspecting optical system is set to a defocus distance deviated from the focus distance, inspection light applied by oblique illumination is applied under different polarization conditions (TE polarization or TM polarization) and where reflected light is collected, a difference is found to be generated, between the pit defect and the bump defect, in the dependency of a minimum value of light intensity of the observed image obtained under TM polarization on the distance between the defect and the objective lens of the inspecting optical system (this dependency will hereinafter be referred to simply as distance dependency).

Figure 13A:
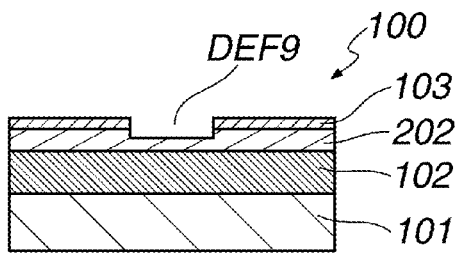
FIG. 13A is a sectional view of the photomask blank shown in FIG. 11A.
Figure 13B:
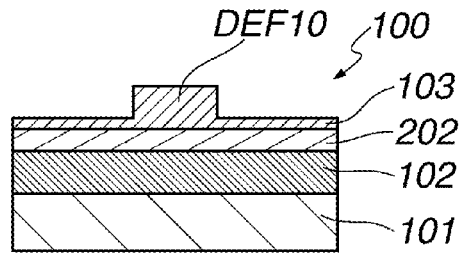
FIG. 13B is a sectional view of the photomask blank shown in FIG. 12B, FIGS. 13C and 13D are diagrams showing sectional profiles of light intensity distribution of inspection images of defects obtained in a positive defocus condition.

FIGS. 13A to 13H illustrate this difference. FIG. 13A is a sectional view of a photomask blank 100 having the pit defect DEF9 depicted in FIG. 11A, and FIG. 13B is a sectional view of a photomask blank 100 having the bump defect DEF10 shown in FIG. 12B.

Figure 13C:
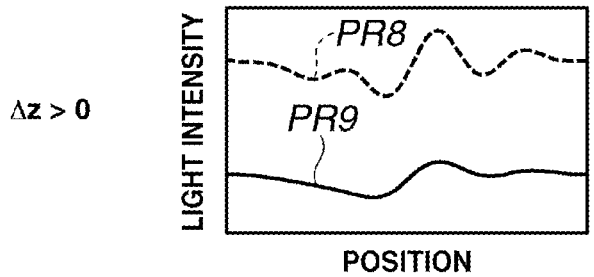
FIGS. 13E and 13F are diagrams showing sectional profiles of light intensity distribution of inspection images of defects obtained at a focus distance.
FIGS. 13G and 13H are diagrams showing sectional profiles of light intensity distribution of inspection images of defects obtained in a negative defocus condition.
Figure 13D:
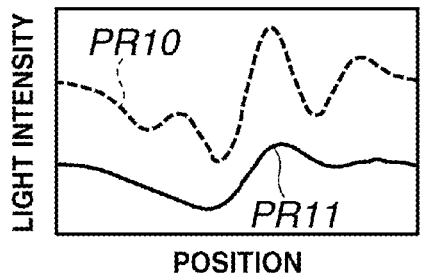
Figure 13E:
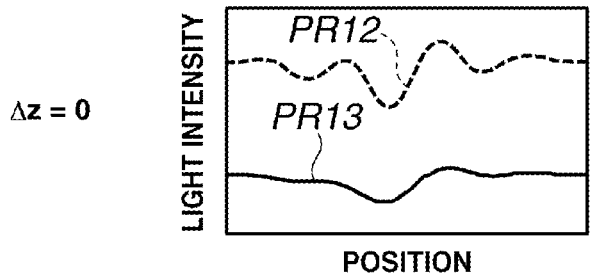
Figure 13F:
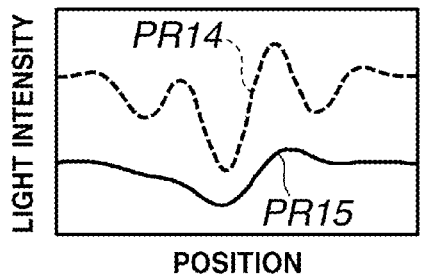

In the case where the inspecting optical system shown in FIG. 3 is used, in inspecting the pit defect DEF9 and the bump defect DEF10, to apply inspection light to a surface of the photomask blank from a left side in the drawings by oblique illumination under TE polarization or TM polarization and where reflected light is collected, if the distance between the defect and the objective lens of the inspecting optical system is set to a focus distance ($\Delta z=0$; note that $\Delta z$ represents the difference from the focus distance, here and hereafter), a sectional profile PR12 (TE polarization) and a sectional profile PR13 (TM polarization) shown in FIG. 13E are obtained as the sectional profile of light intensity distribution of the pit defect DEF9, whereas a sectional profile PR14 (TE polarization) and a sectional profile PR15 (TM polarization) shown in FIG. 13F are obtained as the sectional profile of light intensity distribution of the bump defect DEF10.

In addition, in the case where the distance between the defect and the objective lens of the inspecting optical system is a positive defocus distance, namely, where the mask stage STG with the photomask blank MB mounted thereon is raised to set a positive defocus condition ($\Delta z>0$) nearer than the focus distance, a sectional profile PR8 (TE polarization) and a sectional profile PR9 (TM polarization) shown in FIG. 13C are obtained as the sectional profile of light intensity distribution of the pit defect DEF9, whereas a sectional profile PR10 (TE polarization) and a sectional profile PR11 (TM polarization) shown in FIG. 13D are obtained as the sectional profile of light intensity distribution of the bump defect DEF10.

Figure 13G:
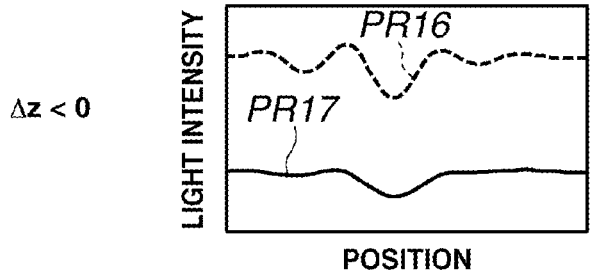
Figure 13H:
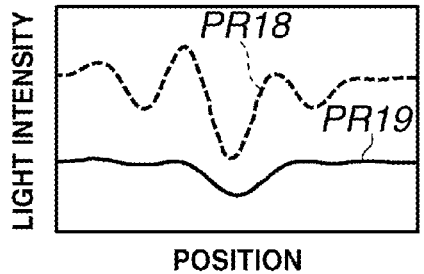

On the other hand, in the case where the distance between the defect and the objective lens of the inspecting optical system is set to a negative focus distance, namely, where the mask stage STG with the photomask blank MB mounted thereon is lowered to set a negative defocus condition ($\Delta z<0$) farther away than the focus distance, a sectional profile PR16 (TE polarization) and a sectional profile PR17 (TM polarization) shown in FIG. 13G are obtained as the sectional profile of light intensity distribution of the pit defect DEF9, whereas a sectional profile PR18 (TE polarization) and a sectional profile PR19 (TM polarization) shown in FIG. 13H are obtained as the sectional profile of light intensity distribution of the bump defect DEF10.

Paying attention to the positional relation between a bright portion and a dark portion in these observed images, it can be said that under any distance conditions and polarization conditions, there is no difference between the pit defect DEF9 and the bump defect DEF10 in the positional relation of bright and dark portions of the inspection image, and, hence, both the defects cannot be discriminated from each other on the basis of the positional relation. However, when distance dependency of a minimum value of light intensity of the observed image obtained under TE polarization and distance dependency of a minimum value of light intensity of the observed image obtained under TM polarization are put to comparison, it is seen that a difference exists between the pit defect DEF9 and the bump defect DEF10. Specifically, for the pit defect DEF9, the minimum value of light intensity of the observed image obtained under TE polarization and the minimum value of light intensity of the observed image obtained under TM polarization are both minimized at the focus distance ($\Delta z=0$), so that the distances at which the minimum value is given coincide with each other. On the other hand, for the bump defect DEF10, the minimum value of light intensity of the observed image obtained under TE polarization is minimized at the focus distance ($\Delta z=0$), whereas the minimum value of light intensity of the observed image obtained under TM polarization is minimized at a positive defocus distance ($\Delta z>0$). This is considered to be attributable to the difference between TE polarized light and TM polarized light in transmission characteristics concerning transmission through the part of the bump defect DEF10 formed of the material transparent to the inspection light. Thus, by changing the focus distance and evaluating the minimum values of light intensity of the inspection images obtained under TM polarization, it is possible to discriminate the pit defect DEF9 and the bump defect DEF10 from each other.

On the other hand, in the case where the bump defect is a bump defect formed by adhesion to the hard mask film of a matter which is low in inspection light transmittance, there is obtained an observed image having a bright portion on the left side and a dark portion on the right side correspondingly to the light intensity distribution of the inspection image of the typical bump defect shown in FIGS. 5A and 5B.

From the foregoing, the rugged shape of a defect in the second film mode can be determined as follows:

(2-1) if a defect portion in the light intensity distribution of the observed image is predominated by a bright portion or composed only of a bright portion, the defect is a pit defect formed only in the film (hard mask film 103) formed from a material substantially transparent to the inspection light;

(2-2) if a defect portion in the light intensity distribution of the observed image has a dark portion on the left side and a bright portion on the right side and the light intensity of the observed image does not have distance dependency, the defect is a pit defect which penetrates the film (hard mask film 103) formed from a material substantially transparent to the inspection light and is further formed also in the film (optical film 202) opaque or semi-transparent to the inspection light;

(2-3) if a defect portion in the light intensity distribution of the observed image has a dark portion on the left side and a bright portion on the right side and the light intensity of the observed image has distance dependency, the defect is a bump defect formed from the same material as that of the film (hard mask film 103) formed from a material substantially transparent to the inspection light; and (2-4) if a defect portion in the light intensity distribution of the observed image has a bright portion on the left side and a dark portion on the right side, the defect is a bump defect formed by adhesion of a matter which is low in inspection light transmittance.

A criterion for determination in the second film mode is different from the criterion in the case of the typical pit defect and bump defect shown in FIGS. 4A, 4B, 5A and 5B, and is peculiar to the case of the second film mode. The criterion for determination in the second film mode is preferable for use in the case where a film being formed from a material substantially transparent to inspection light and serving as an outermost surface layer apart from a transparent substrate and a film being opaque or semi-transparent to the inspection light and being in contact with the transparent substrate side of the above-mentioned film are formed over the transparent substrate and where the film formed of the material substantially transparent to the inspection light has a small thickness, for example, a thickness of 5 to 10 nm.

In the present invention, in the case where a photomask blank includes an optical film formed on a transparent substrate such as quartz substrate and a thin film formed in contact with a side of the optical film opposite to the substrate, the thin film being formed as an outermost surface layer, and where a defect present at a surface portion of the photomask blank is inspected by use of an inspecting optical system to determine the rugged shape of the defect, an inspection treatment procedure and a criterion for determination of the rugged shape of the defect which are peculiar to film mode of the photomask blank are selected and designated. While it is estimated that there exist a multiplicity of inspection treatment procedures and a multiplicity of criteria for determination of the rugged shape of the defect, depending on the film mode of the photomask blanks, the inspection treatment procedures and the criteria for determination can be roughly classified according to the magnitudes of reflectance and transmittance of the thin film and the optical film therebeneath with respect to the inspection light.

The inspection treatment procedure includes one or at least two inspection conditions. The inspection conditions include distance conditions (specifically, a focus distance, or a positive or negative defocus distance) concerning the distance between a defect and the objective lens of the inspecting optical system, and inspection light conditions (specifically, non-polarization, or polarization such as TE polarization and TM polarization). In the case of applying at least two inspection conditions, there may be applied an inspection treatment procedure that includes at least two inspection conditions obtained by changing the just-mentioned conditions. Normally, in the case where determination of the rugged shape of a defect is possible under inspection conditions based on application of the focus distance and non-polarization, only one kind of inspection condition is involved in the inspection treatment procedure. In the case where determination of the rugged shape of a defect is not possible by using only one kind of inspection condition, however, there is applied an inspection treatment procedure which includes not only the one inspection condition but also other different inspection condition or conditions. The inspection treatment procedures and the criteria for determination of the rugged shape of a defect can be determined from data of actual inspection experiments and the results obtained by optical simulations. Specific examples of the criteria included in the criteria for determination include the presence of a bright portion or a dark portion at a defect portion, the layout (positional relation) of the bright portion and the dark portion, a maximum value or minimum value of light intensity, etc. which are obtained from the light intensity distribution of an observed image. In the case where the inspection treatment procedure includes at least two inspection conditions, a method may be adopted wherein, for example, choices such as arithmetic process, defocus control, etc. are prepared in a control unit of the inspecting optical system, and a choice is selected from among the choices and designated upon preparation of a photomask blank to be inspected.

In the defect inspecting method according to the present invention, the inspection light is preferably light having a wavelength of 210 to 550 nm. The range of the defocus distance to be set, which varies depending on the size, depth or height of a defect, is preferably a range of from −300 nm to +300 nm, more preferably from −250 nm to +250 nm. The step width of the defocus distance is preferably approximately 100 nm.

In the present invention, a defect present at a surface portion of a photomask blank including an optical film formed on a substrate and a thin film formed in contact with a side of the optical film opposite to the substrate, the thin film serving as an outermost surface layer, is inspected by use of an inspecting optical system. Examples of the thin film include a hard mask film to be used as a processing aid film for the optical film. In addition, the thin film as an object of inspection preferably has a thickness of up to 10 nm. Note that a lower limit to the thickness of the thin film is normally 3 nm at least.

The defect inspection according to the present invention includes:

(A1) a step of preparing a photomask blank;

(A2) a step of selecting and designating an inspection treatment procedure and a criterion for determination of rugged shape of a defect which correspond to mode of an optical film and a thin film of the photomask blank;

(A3) a step of moving the photomask blank to move the defect into an observation position of an inspecting optical system, applying inspection light to a region including the defect while maintaining a distance between the defect and an objective lens of the inspecting optical system, based on the inspection treatment procedure designated in the step (A2), and collecting reflected light from the region irradiated with the inspection light, as a magnified image of the region, through the inspecting optical system; and (A4) a step of determining the rugged shape of the defect, from light intensity distribution of the magnified image, based on the criterion for determination designated in the step (A2). In the case where the inspection treatment procedure in the step (A2) includes a plurality of kinds of inspection conditions in regard of the step (A3), the step (A3) is carried out sequentially for all the inspection conditions included in the inspection treatment procedure, after which the step (A4) is performed. In addition, the step (A4) preferably includes a treatment of comparing variations in light intensity level at a defect portion of the magnified image with a light intensity level at a portion surrounding the defect, and a treatment of comparing the results of the comparing treatment with the criterion for determination. Note that the step (A4) can be carried out by computing by a computer.

In the case where the inspection treatment procedure in the step (A2) includes only one kind of inspection condition with respect to the step (A3), it is preferable to set the distance between the defect and the objective lens of the inspecting optical system to a focus distance, and to set the inspection light application condition to non-polarization (that the inspection light is non-polarized light). This inspection treatment procedure is particularly preferable for application to defect inspection in the case of the aforementioned first film mode.

On the other hand, in the case where the inspection treatment condition in the step (A2) includes a plurality of kinds of inspection conditions with respect to the step (A3), it is preferable that the inspection conditions include an inspection condition where the distance between the defect and the objective lens of the inspecting optical system is a focus distance and an inspection condition where the distance between the defect and the objective lens is a defocus distance. Preferably, the inspection condition wherein the defocus distance is used includes one or both of an inspection condition wherein a positive defocus distance is used and an inspection condition wherein a negative defocus distance is used.

In addition, in the case where the inspection treatment procedure in the step (A2) includes a plurality of kinds of inspection conditions with respect to the step (A3), it is preferable that the inspection conditions include an inspection condition wherein the inspection light application condition is non-polarization (that the inspection light is non-polarized light) and an inspection condition wherein the inspection light application condition is polarization (that the inspection light is polarized light). Preferably, the inspection condition wherein polarized light is used includes one or both of an inspection condition wherein TE polarized light is used and an inspection condition wherein TM polarized light is used.

Particularly, the plurality of kinds of inspection conditions preferably include, as the distance and the inspection light application condition in the step (A3), an inspection condition wherein a positive defocus distance and TE polarization are used, an inspection condition wherein a positive defocus distance and TM polarization are used, an inspection condition wherein a negative defocus distance and TE polarization are used, and an inspection condition wherein a negative defocus distance and TM polarization are used. Further, the plurality of kinds of inspection conditions may include an inspection condition wherein a focus distance and TE polarization are used, and an inspection condition wherein a focus distance and TM polarization are used. This inspection treatment procedure is particularly preferable for application to defect inspection in the case of the aforementioned second film mode. In this case, it is preferable that, in the step (A3), collection of a magnified image of a region including a defect is conducted under each inspection condition. Particularly, it is preferable that the step (A4) includes a treatment of calculating a minimum value of light intensity level at a defect portion of each magnified image, and a treatment of comparing the result of this calculating treatment with a criterion of determination.

The inspection light is preferably applied by oblique illumination wherein the optical axis of the inspection light is inclined at a predetermined angle in relation to a normal to that surface of the thin film which is irradiated with the inspection light. In addition, it is preferable that, in the step (A3), the photomask blank is mounted on a stage capable of being moved in an in-plane direction of the photomask blank, and the stage is moved in the in-plane direction to bring the defect and the objective lens of the inspecting optical system close to each other. By inspecting a defect by the method including the aforementioned steps (A1) to (A4), it is possible to determine the rugged shape of the defect more accurately.

Figure 14:
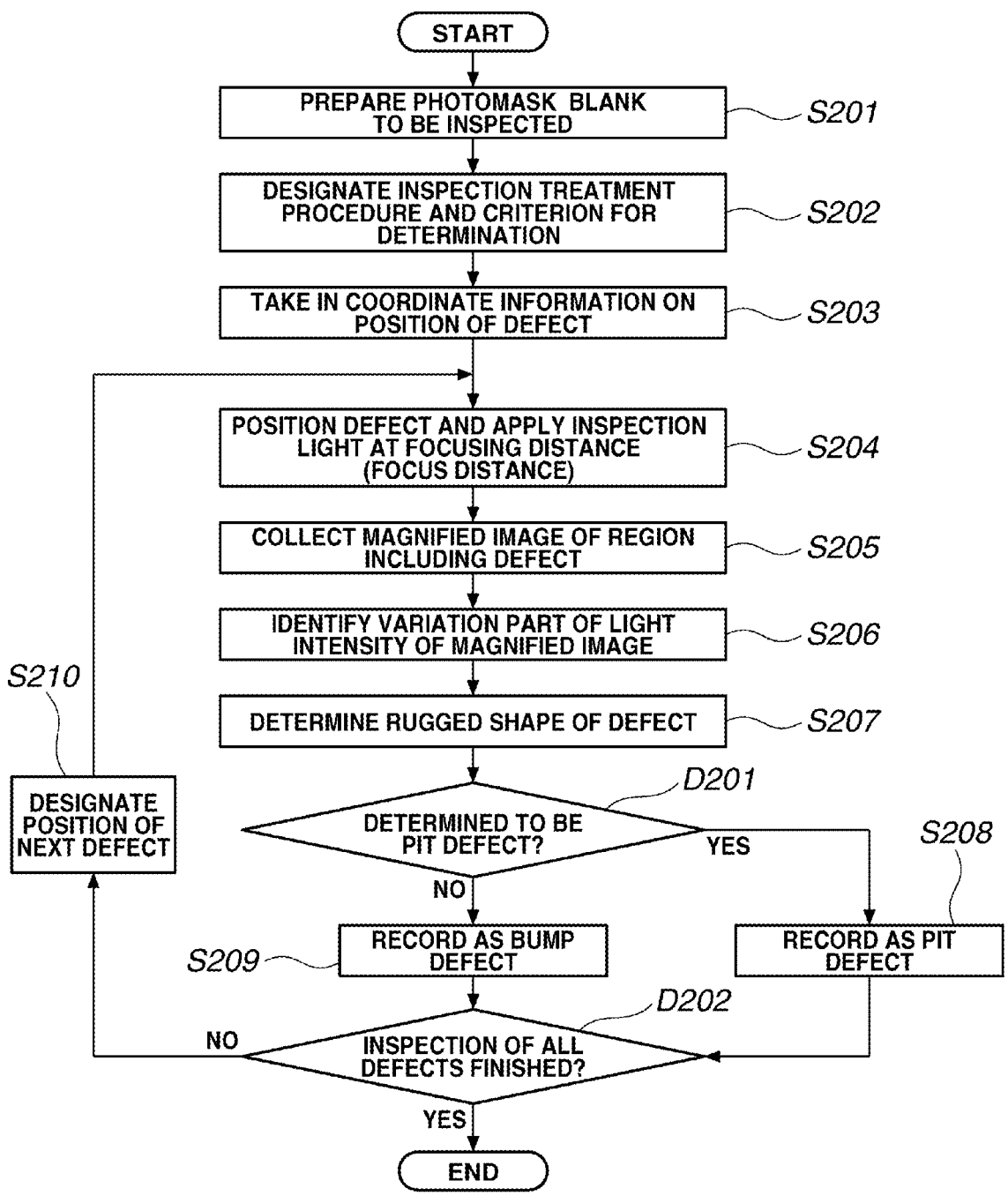
FIG. 14 is a flow chart showing an example of steps of a defect inspecting method for a photomask blank.

Now, the defect inspecting method according to the present invention will be described more specifically below, along a flow chart shown in FIG. 14. First, as the step (A1), a photomask blank as an object of inspection that has a defect (photomask blank to be inspected) is prepared (step S201).

Next, as the step (A2), an intrinsic inspection treatment procedure and an intrinsic criterion for determination of the rugged shape of a defect that correspond to film mode of the photomask blank to be inspected are selected and designated (step S202). Subsequently, coordinate information on the position of a defect present on the photomask blank is taken in (step S203). As the defect position coordinates, defect position coordinates which have been preliminarily identified by known defect inspection can be used.

Next, as the step (A3), the position of the defect is matched to an inspection position of the inspecting optical system, the defect and the objective lens of the inspecting optical system are brought close to each other, the distance between the defect and the objective lens of the inspecting optical system is set to a focus distance, then, while maintaining the focus distance, inspection light is applied through the objective lens, for example, from an oblique direction (in the method shown in the flow chart, from a left side of the defect) (step S204), and reflected light from a region irradiated with the inspection light is collected through the objective lens of the inspecting optical system as a magnified image of a region including the defect (step S205). The position matching may be conducted by a method wherein the photomask blank as an object to be inspected is placed on a stage capable of being moved in an in-plane direction of the photomask blank, and the stage is moved in the in-plane direction on the basis of position coordinates of the defect on the photomask blank to be inspected, to bring the defect and the objective lens of the inspecting optical system close to each other. Note that the step (A3) is carried out also under other inspection condition or conditions, as required, depending on the inspection treatment procedure.

Subsequently, from light intensity distribution (image data (inspection image) and a sectional profile, etc.) of the magnified image thus collected, a variation portion of light intensity of the defect portion is identified (step S206), after which, as the step (A4), the rugged shape of the defect is determined (step S207) according to the criterion for determination of the rugged shape that has been designated in step S202. If the defect is determined to be a pit defect in step S207, defect information is recorded as a pit defect (decision D201, step S208), whereas if the defect is not determined to be a pit defect in step S207, defect information is recorded as a bump defect (decision D201, step S209). Next, it is determined whether or not inspection has been finished for all the defects based on the defect position coordinate information preliminarily taken in (decision D202), and, if inspection has not yet been finished for all the defects, after new defect positions are specified (step S210), the control process returns to the step S204, and collection of inspection image data and determination of the rugged shape of a defect are repeated. Then, if it is determined that inspection has been finished for all the defects preliminarily taken in (decision D202), the defect inspection is ended.

Figure 15:
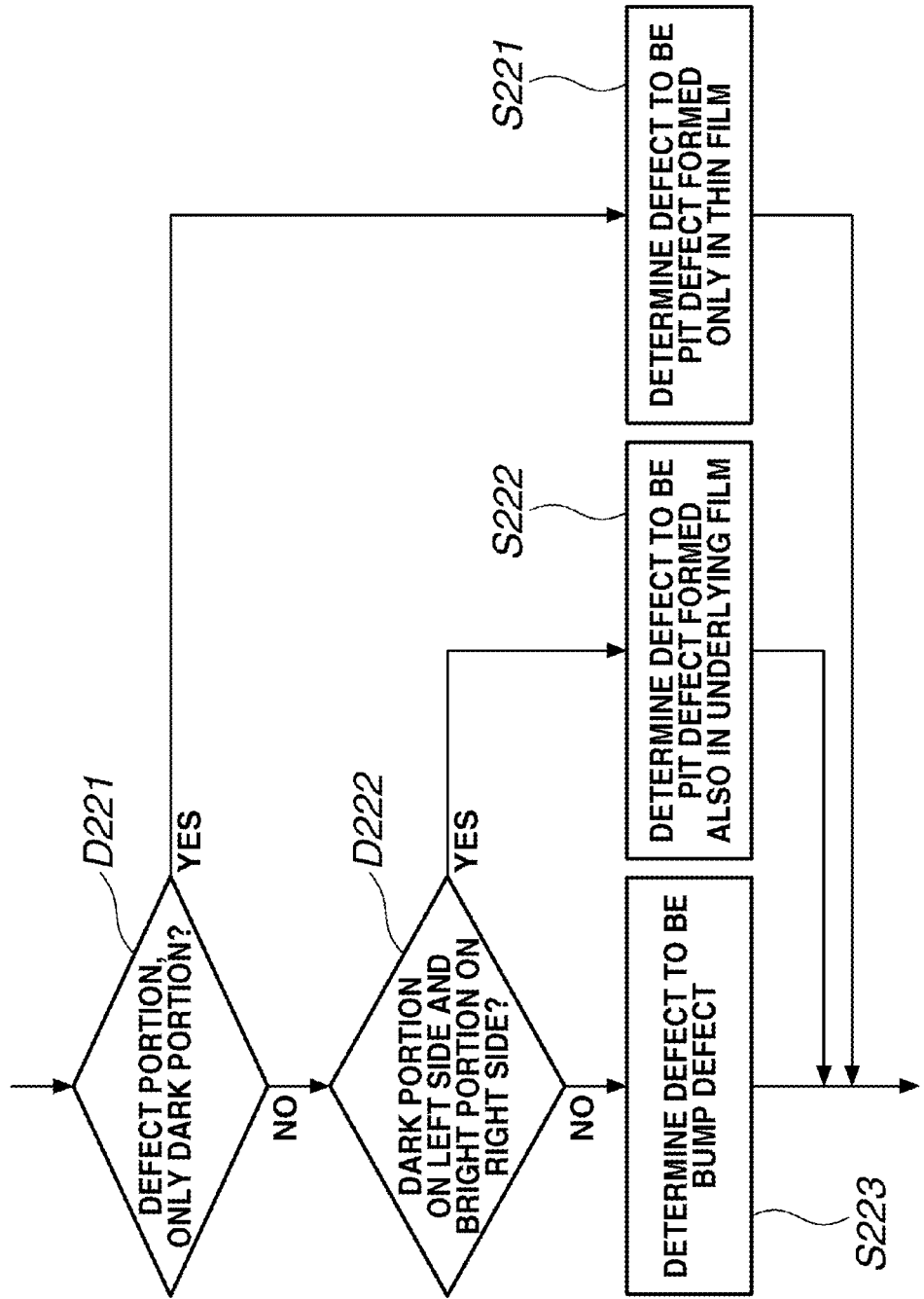
FIG. 15 is a flow chart showing an example of steps for determining rugged surface shape of a defect portion of a photomask blank.

In the next, as a specific example of the step (A4) (step S207) which is a determination step according to the criterion for determination of the rugged shape, a determination step preferable for use in inspection of a photomask blank in the first film mode will be described below, along a flow chart shown in FIG. 15. FIG. 15 shows details of the step S207 in the flow chart shown in FIG. 14.

First, in the first decision step (decision D221), it is examined whether or not the light intensity distribution corresponding to a defect portion, among image data on the magnified image obtained in the step S206, has only a dark portion, and if the light intensity distribution has only a dark portion, the defect in question is determined to be a pit defect formed only in the thin film (step S221). Next, if the light intensity distribution is determined not to have only a dark portion in the decision D221, the layout of a bright portion and a dark portion is examined in the next decision step (decision D222). If the layout includes a dark portion on the left side and a bright portion on the right side, the defect in question is determined to be a pit defect which penetrates the thin film and is further formed also in the underlying film (optical film) (step S222), whereas if the layout is otherwise, the defect in question is determined to be a bump defect (step S223). In the case of a pit defect formed only in the thin film in the first film mode, the defect portion of the magnified image has only a dark portion, which is different from the light intensity distribution (sectional profile PR1) of the typical pit defect shown in FIG. 4B. This is a characteristic feature of the criterion for determination of the rugged shape in the first film mode.

Figure 16:
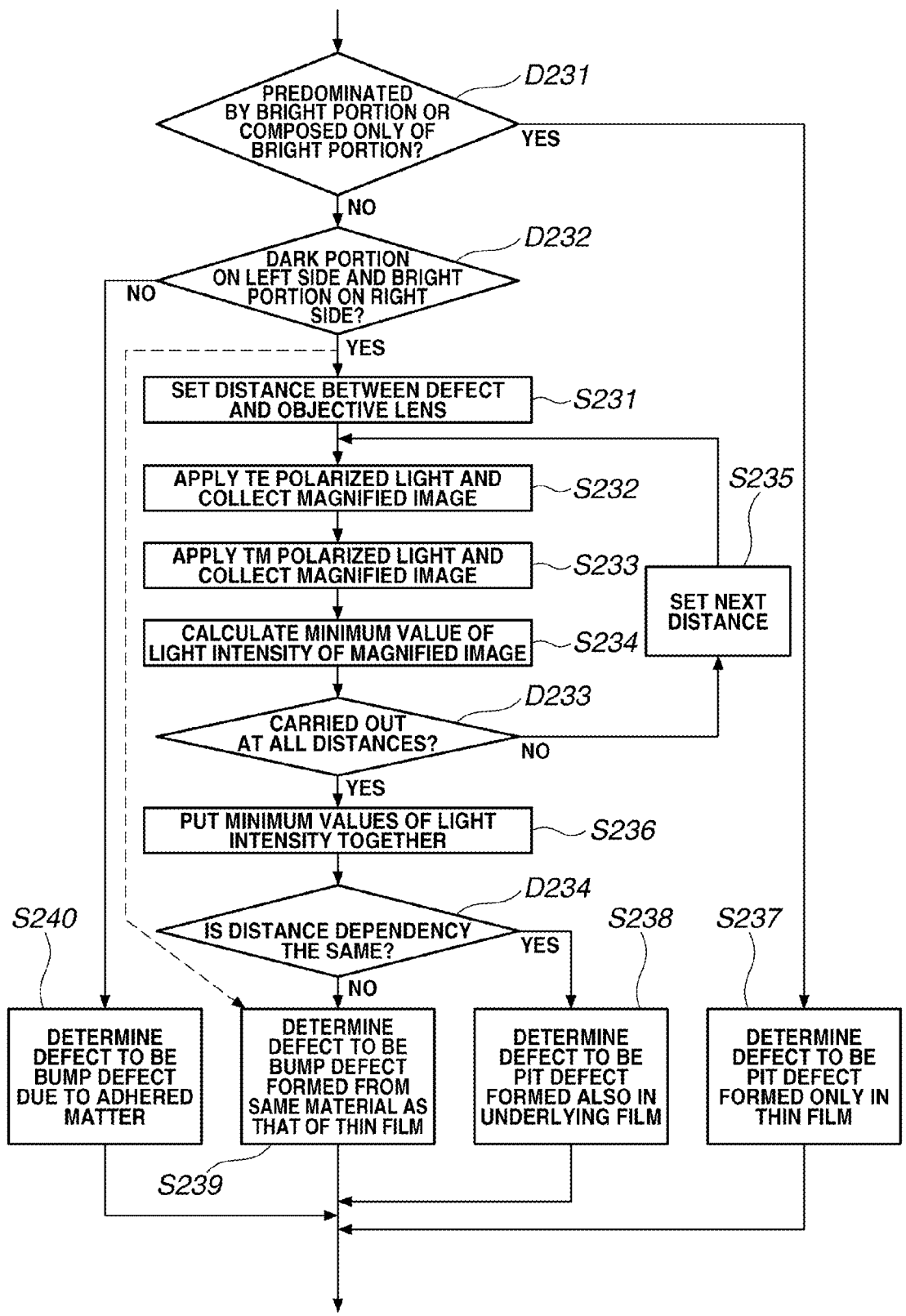
FIG. 16 is a flow chart showing another example of steps for determining rugged surface shape of a defect portion of a photomask blank.

In addition, as a specific examples of the step (A4) (step S207) which is a determination step according to the criterion for determination of the rugged shape, a determination step preferable for use in inspection of a photomask blank in the second film mode will be described below, along a flow chart shown in FIG. 16. FIG. 16 shows details of the step S207 in the flow chart shown in FIG. 14.

First, in the first decision step (decision D231), it is examined whether or not the light intensity distribution corresponding to a defect portion, among image data on the magnified image obtained in the step S206, is predominated by a bright portion or composed only of a bright portion, and if the light intensity distribution is predominated by a bright portion or composed only of a bright portion, the defect in question is determined to be a pit defect formed only in the thin film (step S237). Next, if it is determined in the decision D231 that the light intensity distribution is not predominated by a bright portion or composed only of a bright portion, the layout of a bright portion and a dark portion is examined in the next decision step (decision D232), and if the layout is found to include a dark portion on the left side and a bright portion on the right side, the control process proceeds to step S231.

If it is determined in the decision step D232 that the layout includes a dark portion on the left side and a bright portion on the right side, inspection image of the defect is further collected under a new inspection condition obtained through one or both of a condition change wherein the distance between the defect and the objective lens of the inspecting optical system is set to a defocus distance (a positive defocus distance or a negative defocus distance) deviated from the focus distance and a change wherein illumination light in the inspecting optical system shown in FIG. 3 is set to TE polarization or TM polarization, and, thereafter, the control process proceeds to determination of the rugged shape of the defect. For instance, after the defocus distance is set to one distance (initial value) (step S231), collection of a magnified image by illumination with TE polarized light is conducted at the thus set defocus distance (step S232), then collection of a magnified image by illumination with TM polarized light is conducted (step S233) (note that the step S232 and the step S233 may be interchanged), and minimum values of light intensity are calculated from the light intensity distributions of the magnified images (step S234). Note that, in this instance, collection of a magnified image by illumination with non-polarized light may be conducted, as required. Next, it is determined whether or not the collection of a magnified image has been conducted at all the predetermined settings of the defocus distance (decision D233), and if the collection has not yet been conducted at all the settings, the distance between the defect and the objective lens of the inspecting optical system is set to other distance (next distance) (step S235), and the steps S232 to S234 are repeated. Note that, in this instance, collection of a magnified image at the focus distance may be performed, as required. When inspection under all the inspection conditions is finished, the minimum values of light intensity obtained under respective distances and illumination conditions are put together (step S236). Subsequently, in decision step D234, a distance at which a smallest one of the minimum values of light intensity obtained under TE polarization is exhibited and a distance at which a smallest one of the minimum values of light intensity obtained under TM polarization is exhibited are compared with each other, to thereby evaluate distance dependency. If the smallest minimum values thus compared are substantially equal, the defect in question is determined to be a defect which penetrates the thin film and is further formed also in the underlying optical film (step S238); if the smallest minimum values compared are different, the defect in question is determined to be a bump defect formed from the same material as that of the thin film (step S239).

On the other hand, if it is determined in the decision step D232 that the layout does not include a dark portion on the left side and a bright portion on the right side, the defect in question is determined to be a bump defect formed by adhesion of a matter low in transmittance to the inspection light (step S240).

Note that the steps from the step S231 to the decision step D234 are steps for discrimination between a pit defect which penetrates the thin film and is formed also in the underlying optical film and a bump defect formed from the same material as that of the thin film. In the case where the underlying optical film is free of defects and it is needed only to determine the rugged shape of a defect in the thin film, the steps from the step S231 to the decision step D234 are unnecessary. In this case, if the layout is found in the decision step S232 to include a dark portion on the left side and a bright portion on the right side, the control process proceeds along the chain-line arrow in FIG. 16, and the defect in question can be determined to be a bump defect formed from the same material as that of the thin film. In the second film mode, for a pit defect formed only in the thin film, the defect portion of the magnified image substantially has only a bright portion, which is different from the light intensity distribution (sectional profile PR1) of the typical pit defect shown in FIG. 4B. In addition, for a bump defect formed from the same material as that of the thin film, the relevant light intensity distribution is different from the light intensity distribution (sectional profile PR2) of the typical bump defect shown in FIG. 5B. These are characteristic features of the criterion for determination of the rugged shape in the second film mode. According to the present inspection treatment procedure and criteria for determination, therefore, a bump defect can be correctly determined without being erroneously determined to be a pit defect.

According to the defect inspecting method of the present invention, in the case where a thin film such as a hard mask film, for example, a thin film having a thickness of up to 10 nm is formed at an outermost surface portion of the photomask blank, the rugged shape of a defect can be discriminated with high reliability, by using an inspection treatment procedure and a criterion for determination of the rugged shape which are peculiar to the film mode, collecting the inspection image according to the predetermined inspection treatment procedure, and carrying out a treatment for determining the rugged shape.

Where the defect inspecting method of the present invention by which the rugged shape of a defect can be discriminated highly reliably is applied to a photomask blank production process, photomask blanks having a pit defect, particularly a pinhole defect, can be extracted highly reliably, and photomask blanks having no pit defect such as a pinhole defect can be sorted out. In addition, information on the rugged shape of a defect obtained by the defect evaluation method of the present invention can be imparted to a photomask blank by accompaniment of an inspection card, for example. Further, the photomask blanks having no pit defect such as pinhole defect can also be sorted out based on the information imparted to the photomask blanks. Conventionally, a bump defect due to an adhered matter might be determined to be a pit defect by optical inspection, and there has been a high possibility that a photomask blank having a defect that is not necessarily a fatal defect might be rejected as a defective, thereby causing a lowering in the yield. By the defect inspecting method of the present invention, on the other hand, photomask blanks having a pit defect that is a fatal defect can be rejected selectively, and, therefore, photomask blanks conforming to product specifications can be provided in a high yield.

EXAMPLES

The present invention will be described specifically below, referring to Examples, however the present invention is not to be limited to the following Examples.

Example 1

Defect inspection of photomask blanks having a pit defect and a bump defect in the first film mode was carried out. In this example, a criterion for determination in the first film mode was applied. As an inspecting optical system, the inspecting optical system shown in FIG. 3 was used, with a numerical aperture NA of 0.75 and an inspection wavelength of 248 nm. Oblique illumination was adopted in which inspection light is applied toward a defect on the photomask blank from a left upper side in the figure at an average incidence angle of 38 degrees. Note that an inspection light application condition was non-polarization.

Figure 17A:
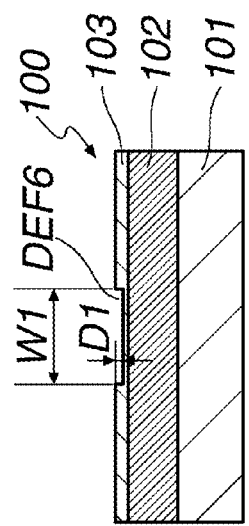
FIG. 17A is a sectional view of a photomask blank having a pit defect formed only in a hard mask film in Example 1.
Figure 17B:
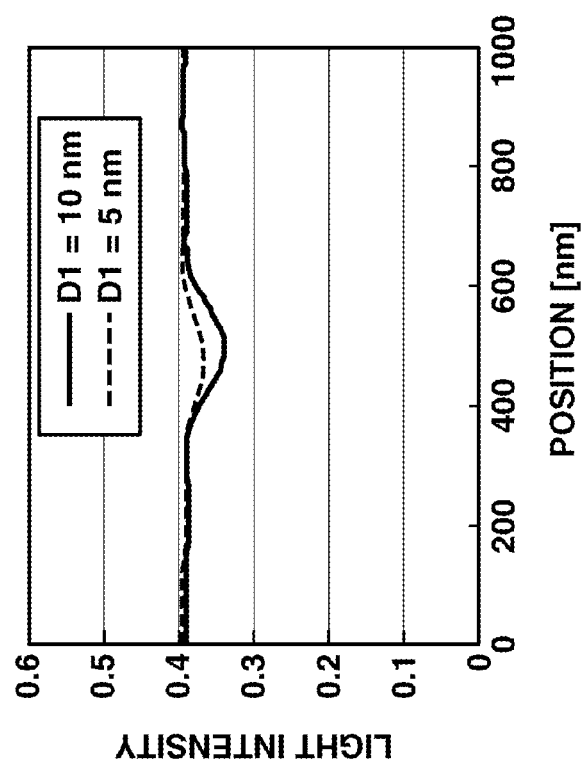
FIG. 17B is a diagram showing a sectional profile of light intensity distribution of an inspection image obtained at a focus distance.

A photomask blank 100 illustrated in FIG. 17A has a structure in which an optical film 102 formed from an MoSi material and a hard mask film 103 formed from a Cr material in a thickness of 10 nm are formed over a quartz substrate 101 transparent to inspection light, with a pit defect DEF6 such as a pinhole defect being present in the hard mask film 103. Sectional profiles of light intensity of inspection images obtained at a focus distance when the width W1 of the pit defect DEF6 is 100 nm and the depth D1 is either of 5 nm (a pit defect which does not penetrate the hard mask film 103) and 10 nm (a pit defect which penetrates the hard mask film 103) are depicted in FIG. 17B. In the case of a fatal pit defect, particularly a pinhole defect, formed only in the hard mask film 103, no bright portion appears but only a dark portion appears in a defect portion of the sectional profile of light intensity.

A photomask blank 100 shown in FIG. 18A has a structure in which an optical film 102 formed from an MoSi material and a hard mask film 103 formed from a Cr material in a thickness of 10 nm are formed over a quartz substrate 101 transparent to inspection light, with a pit defect DEF11 such as a pinhole defect being present in the optical film 102 and the hard mask film 103. Sectional profiles of light intensity of inspection images obtained at a focus distance when the width W1 of the pit defect DEF11 is 100 nm and the depth D1 is 30 nm and 40 nm (pit defects which penetrate the hard mask film 103 and are further formed also in the optical film 102) are shown in FIG. 18B. In the case of a fatal pit defect, particularly a pinhole defect, which penetrates the hard mask film 103 and is further formed also in the optical film 102, a defect portion of the sectional profile of light intensity has a dark portion on the left side and a bright portion on the right side. Thus, although the intensity level varies depending on the depth of the pit defect, the same positional relation between bright and dark portions as that in the light intensity distribution (sectional profile PR1) of the typical pit defect shown in FIG. 4B is obtained.

Figure 19A:
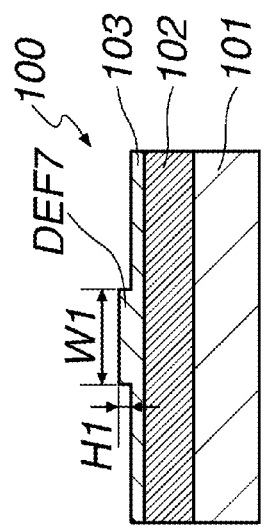
FIG. 19A is a sectional view of a photomask blank having a bump defect in Example 1.
Figure 19B:
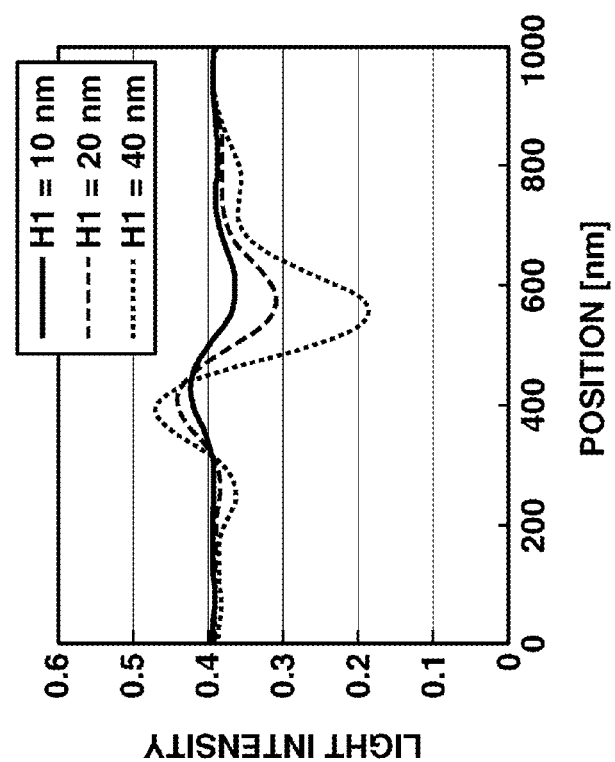
FIG. 19B is a diagram showing a sectional profile of light intensity distribution of an inspection image obtained at a focus distance.

A photomask blank 100 illustrated in FIG. 19A has a structure in which an optical film 102 formed from an MoSi material and a hard mask film 103 formed from a Cr material in a thickness of 10 nm are formed over a quartz substrate 101 transparent to inspection light, with a bump defect DEF7 being present on the hard mask film 103. Sectional profiles of light intensity of inspection images obtained at a focus distance when the width W1 of the bump defect DEF7 is 100 nm and the height H1 is 10 nm, 20 nm and 40 nm are shown in FIG. 19B. In the case of a bump defect, a defect portion of the sectional profile of light intensity has a bright portion on the left side and a dark portion on the right side. Thus, although the intensity level varies depending on the height of the bump defect, the same positional relation between bright and dark portions as that in the light intensity distribution (sectional profile PR2) of the typical bump defect shown in FIG. 5B is obtained.

From the foregoing, it is seen that in the case of a photomask blank in which a thin film such as a hard mask film of a high-reflectance material is formed over an optical film, the rugged shape of a defect present in the photomask blank can be correctly determined according to a criterion for determination as follows:

if the light intensity distribution of the inspection image of the defect obtained at a focus distance has only a dark portion or has a dark portion on the left side and a bright portion on the right side, the defect in question is a pit defect; and if the light intensity distribution has a bright portion on the left side and a dark portion on the right side, the defect in question is a bump defect.

Example 2

Defect inspection of photomask blanks having a pit defect and a bump defect in the second film mode was carried out. In this example, a criterion for determination in the second film mode was applied. As an inspecting optical system, the inspecting optical system shown in FIG. 3 was used, with a numerical aperture NA of 0.75 and an inspection wavelength of 248 nm. Oblique illumination was adopted in which inspection light is applied toward a defect on the photomask blank from a left upper side in the figure at an average incidence angle of 38 degrees. Note that an inspection light application condition was non-polarization, unless specified otherwise.

Figure 20A:
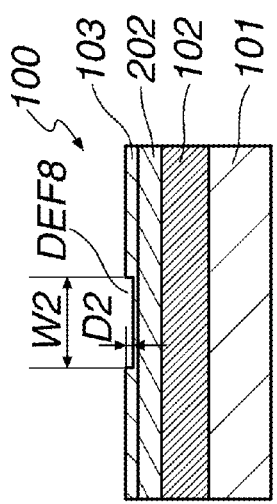
FIG. 20A is a sectional view of a photomask blank having a pit defect formed only in a hard mask film in Example 2.
Figure 20B:
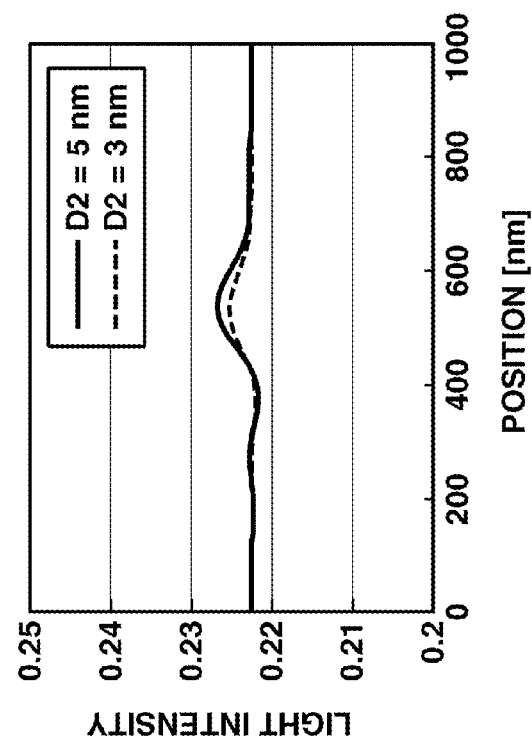
FIG. 20B is a diagram showing a sectional profile of light intensity distribution of an inspection image obtained at a focus distance.

A photomask blank 100 illustrated in FIG. 20A has a structure in which an optical film 102 formed from an MoSi material, an optical film 202 formed from a Cr material, and a hard mask film 103 formed from silicon oxide in a thickness of 5 nm are formed over a quartz substrate 101 transparent to inspection light, with a pit defect DEF8 such as a pinhole defect being present in the hard mask film 103. Sectional profiles of light intensity of inspection images obtained at a focus distance when the width W2 of the pit defect DEF8 is 100 nm and the depth D2 is 3 nm (a pit defect which does not penetrate the hard mask film 103) and 5 nm (a pit defect which penetrates the hard mask film 103) are shown in FIG. 20B. In the case of a fatal pit defect, particularly a pinhole defect, formed only in the hard mask film 103, a bright portion is predominant, or a dark portion does not appear but only a bright portion appears, in a defect portion of the sectional profile of light intensity.

Figure 21A:
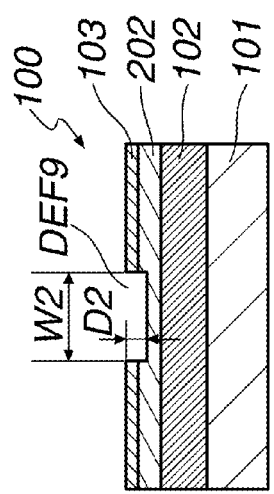
FIG. 21A is a sectional view of a photomask blank having a pit defect formed in a hard mask film and an optical film in Example 2.
Figure 21B:
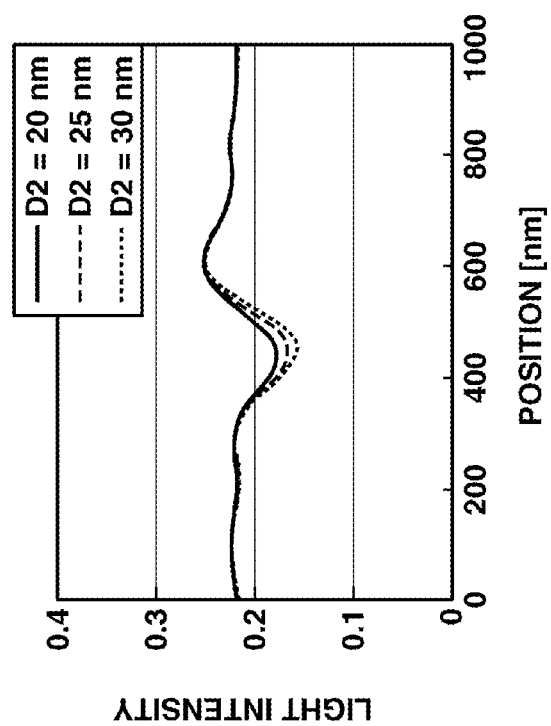
FIG. 21B is a diagram showing a sectional profile of light intensity distribution of an inspection image obtained at a focus distance.

A photomask blank 100 shown in FIG. 21A has a structure in which an optical film 102 formed from an MoSi material, an optical film 202 formed from a Cr material, and a hard mask film 103 formed from silicon oxide in a thickness of 5 nm are formed over a quartz substrate 101 transparent to inspection light, with a pit defect DEF9 such as a pinhole defect being present in the optical film 202 and the hard mask film 103. Sectional profiles of light intensity of inspection images obtained at a focus distance when the width W2 of the pit defect DEF9 is 100 nm and the depth D1 is 20 nm, 25 nm and 30 nm (pit defects which penetrate the hard mask film 103 and are further formed also in the optical film 102) are shown in FIG. 21B. In the case of a fatal pit defect, particularly a pinhole defect, formed to penetrate the hard mask film 103 and further formed also in the optical film 102, a defect portion of the sectional profile of light intensity has a dark portion on the left side and a bright portion on the right side. Thus, although the intensity level varies depending on the depth of the pit defect, the same positional relation between bright and dark portions as that in the light intensity distribution (profile PR1) of the typical pit defect shown in FIG. 4B is obtained.

Figure 22A:
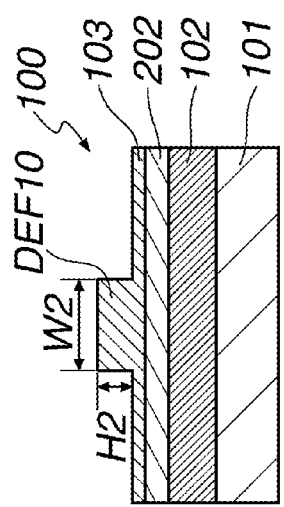
FIG. 22A is a sectional view of a photomask blank having a bump defect formed of the same material as that of a hard mask film in Example 2.
Figure 22B:
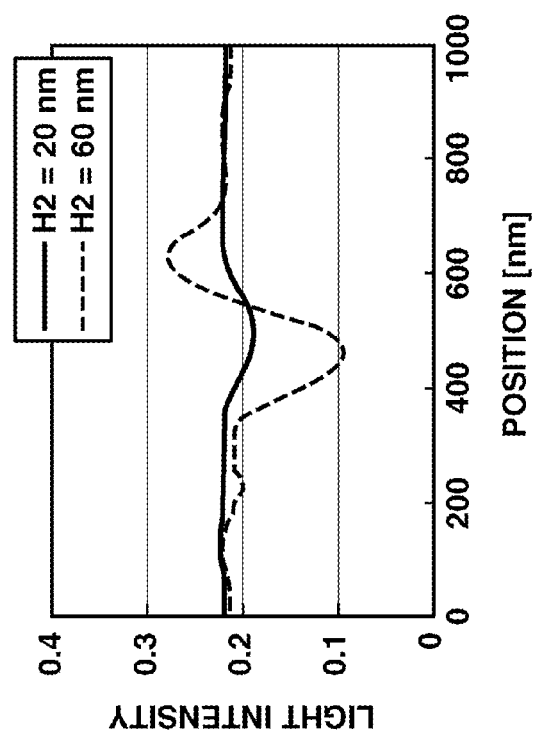
FIG. 22B is a diagram showing a sectional profile of light intensity distribution of an inspection image obtained at a focus distance.

A photomask blank 100 illustrated in FIG. 22A has a structure in which an optical film 102 formed from an MoSi material, an optical film 202 formed from a Cr material, and a hard mask film 103 formed from silicon oxide in a thickness of 5 nm are formed over a quartz substrate transparent to Inspection light, wherein a bump defect DEF10 formed from the same material as that of the hard mask film 103 is present on the hard mask film 103. Sectional profiles of light intensity of inspection images obtained at a focus distance when the width W2 of the bump defect DEF10 is 100 nm and the height H2 is 20 nm and 60 nm are shown in FIG. 22B. In the case of this bump defect, a defect portion of the sectional profile of light intensity has a dark portion on the left side and a bright portion on the right side, which does not correspond to the light intensity distribution (sectional profile PR2) of the typical bump defect of FIG. 5B. Moreover, in terms of the positional relation between a bright portion and a dark portion of the light intensity distribution, the positional relation relevant to the bump defect shown in FIG. 22A is the same as the positional relation relevant to the pit defect shown in FIG. 21A. Based on the positional relation between bright and dark portions of light intensity distribution, therefore, it is impossible to discriminate the fatal pit defect shown in FIG. 21A and the bump defect shown in FIG. 22A.

Figure 23A:
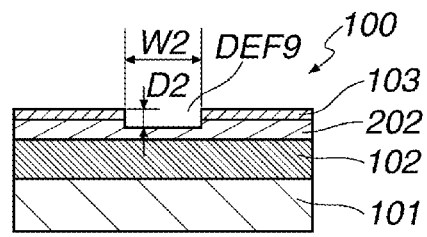
FIG. 23A is a sectional view of a photomask blank having a pit defect formed in a hard mask film and an optical film in Example 2.
Figure 23B:
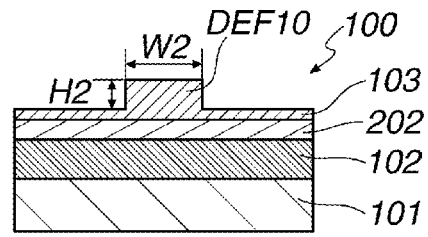
FIG. 23B is a sectional view of a photomask blank having a bump defect formed of the same material as that of a hard mask film in Example 2.

In view of this, with respect to the pit defect shown in FIG. 21A and the bump defect shown in FIG. 22A, observed images were collected at a plurality of defocus distances, and variations in light intensity of the observed images were examined. FIG. 23A is a sectional view of a photomask blank having the pit defect DEF9 of FIG. 21A, and FIG. 23B is a sectional view of a photomask blank having the bump defect DEF10 of FIG. 22A. The pit defect DEF9 was formed to have a width W2 of 100 nm and a depth D2 of 25 nm, whereas the bump defect DEF10 was formed to have a width W2 of 100 nm and a height H2 of 60 nm. In addition, FIGS. 23C to 23H are diagrams showing sectional profiles of light intensity distribution of observed images obtained at two defocus distances and a focus distance.

Figure 23C:
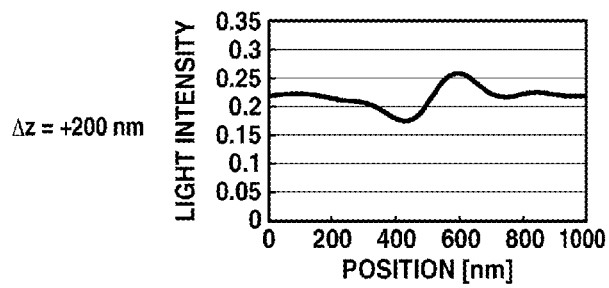
FIGS. 23C and 23D are diagrams showing sectional profiles of light intensity distribution of inspection images of defects obtained at a defocus distance of +200 nm.
Figure 23D:
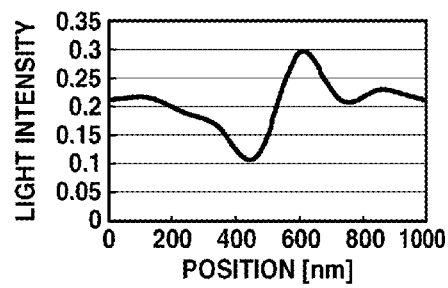
Figure 23E:
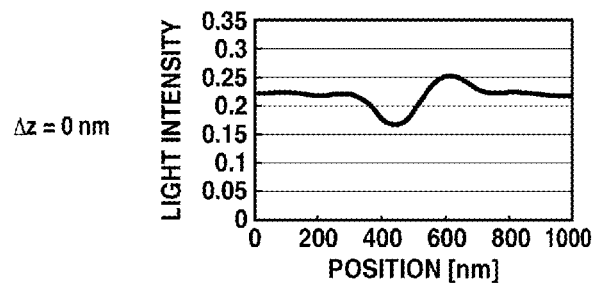
FIGS. 23E and 23F are diagrams showing sectional profiles of light intensity distribution of inspection images of defects obtained at a focus distance.
Figure 23F:
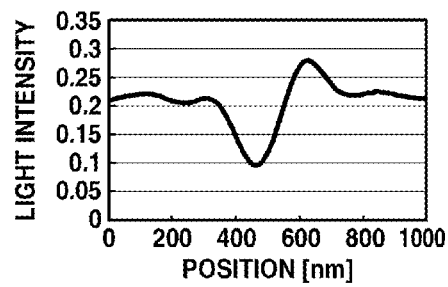
Figure 23G:
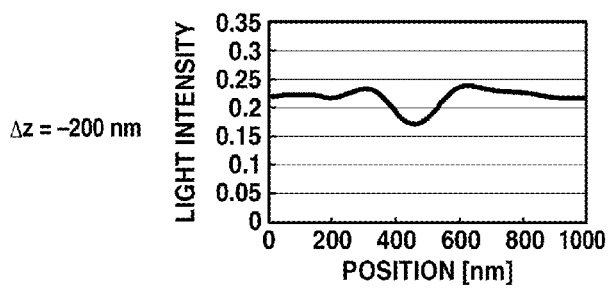
FIGS. 23G and 23H are diagrams showing sectional profiles of light intensity distribution of inspection images of defects obtained at a defocus distance of −200 nm.
Figure 23H:
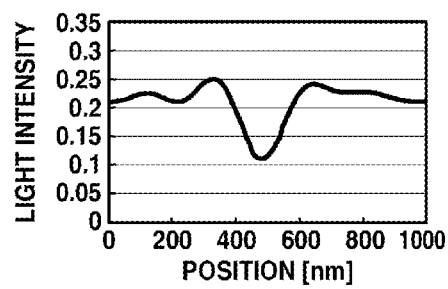

Sectional profiles of light intensity distribution of observed images of the pit defect DEF9 obtained when the distance Δz is +200 nm, 0 nm, and −200 nm, respectively, are shown in FIGS. 23C, 23E, and 23G. Besides, sectional profiles of light intensity distribution of observed images of the bump defect DEF10 obtained when the distance Δz is +200 nm, 0 nm, and −200 nm, respectively, are shown in FIGS. 23D, 23F, and 23H. From these results it is seen that even with comparison at a defocus distance, the pit defect DEF9 and the bump defect DEF10 cannot be discriminated from each other, based on the positional relation between bright and dark portions of the light intensity distribution of the observed images.

In view of the above, observed images were collected at a focus distance and a plurality of defocus distances, with an inspection light application condition changed to TE polarization or TM polarization, and, also in the case of non-polarization, observed images were further collected with the distance Δz set to a defocus distance other than +200 nm and −200 nm, after which minimum values of light intensity distribution of the observed images were determined. FIGS. 24A and 24B are diagrams showing distance dependency of minimum values of light intensity distribution of the observed images of the pit defect DEF9 and the bump defect DEF10, respectively. A comparison of FIG. 24A with FIG. 24B shows that in the case of the pit defect DEF9, the minimum values of light intensity distribution of the observed images obtained under non-polarization, TE polarization and TM polarization are all minimized at the focus distance (Δz=0). On the other hand, in the case of the bump defect DEF10, while the minimum values of light intensity distribution of the observed image obtained under non-polarization and TE polarization are both minimized at the focus distance (Δz=0), the minimum value of light intensity distribution of the observed image obtained under TM polarization is minimized at a defocus distance Δz of approximately +200 nm. This is considered to be attributable to a difference between TE polarized light and TM polarized light in transmission characteristics at the time of transmission through the part of the bump defect DEF10 formed from a material transparent to inspection light. Thus, by evaluating the distance dependency of the minimum value of light intensity distribution of the inspection image obtained under TM polarization while changing the distance between the defect and the objective lens of the inspecting optical system, it is possible to discriminate the pit defect DEF9 and the bump defect DEF10 from each other.

Figure 25A:
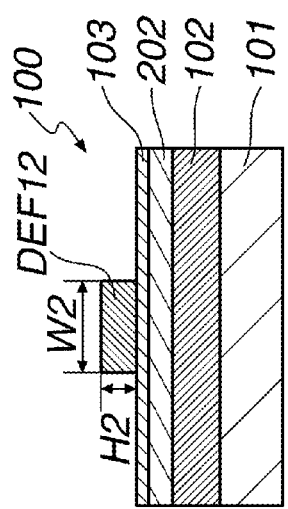
FIG. 25A is a sectional view of a photomask blank having a bump defect formed by adhesion of a matter which is low in inspection light transmittance in Example 2.
Figure 25B:
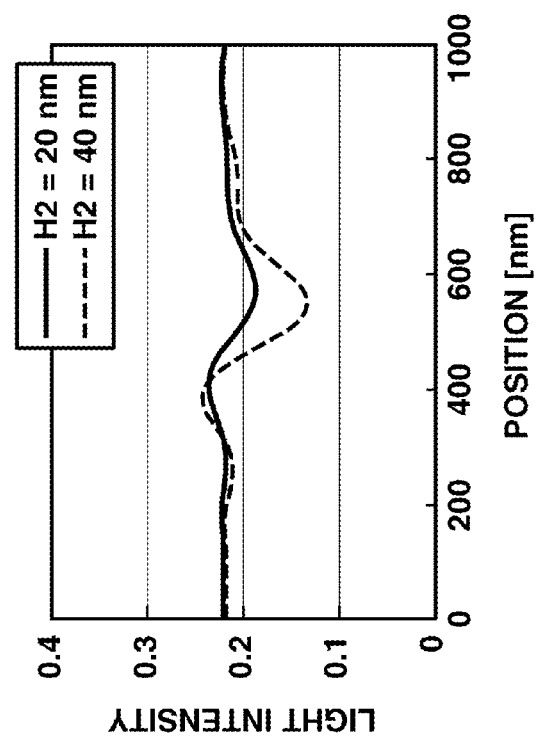
FIG. 25B is a diagram showing a sectional profile of light intensity distribution of an inspection image obtained at a focus distance.

A photomask blank 100 illustrated in FIG. 25A has a structure in which an optical film 102 formed from an MoSi material, an optical film 202 formed from a Cr material, and a hard mask film 103 formed from silicon oxide in a thickness of 5 nm are formed over a quartz substrate transparent to inspection light, wherein a bump defect DEF12 formed by adhesion of a matter low in transmittance to the inspection light is formed on the hard mask film 103. Sectional profiles of light intensity of observed images obtained at a focus distance when the width W2 of the bump defect DEF12 is 100 nm and the height H2 is 20 nm and 40 nm are shown in FIG. 25B. In the case of the bump defect formed by adhesion of a matter low in transmittance to the inspection light, a defect portion of the sectional profile of light intensity has a bright portion on the left side and a dark portion on the right side. Thus, although the intensity level varies depending on the height of the bump defect, the same positional relation between bright and dark portions as that in the light intensity distribution (sectional profile PR2) of the typical bump defect shown in FIG. 5B is obtained.

From the foregoing, it is seen that in the case of a photomask blank in which a thin film such as a hard mask film of a material substantially transparent to inspection light is formed over an optical film, the rugged shape of a defect present in the photomask blank can be correctly determined according to a criterion for determination as follows:

if the light intensity distribution of the inspection image of the defect obtained at a focus distance is predominated by a bright portion or composed only of a bright portion, or if a defect portion of the light intensity distribution of the inspection image of the defect has a dark portion on the left side and a bright portion on the right side and light intensity of the observed image is free of distance dependency, the defect in question is a pit defect; and if a defect portion of the light intensity distribution of the inspection image of the defect has a dark portion on the left side and a bright portion on the right side and light intensity of the observed image has distance dependency, or if the light intensity distribution of the inspection image of the defect obtained at a focus distance has a bright portion on the left side and a dark portion on the right side, the defect in question is a bump defect.

Japanese Patent Application No. 2015-174684 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method of inspecting a defect present at a surface portion of a photomask blank by use of an inspecting optical system, the photomask blank including an optical film formed on a substrate, and a thin film formed in contact with a side of the optical film opposite to the substrate, the thin film being formed as an outermost surface layer, the method comprising:
    (A1) a step of preparing the photomask blank;
    (A2) a step of selecting and designating an inspection treatment procedure and a criterion for determination of rugged shape of the defect which correspond to mode of the optical film and the thin film of the photomask blank;
    (A3) a step of moving the photomask blank to move the defect into an observation position of the inspecting optical system,
        applying inspection light to a region including the defect while maintaining a distance between the defect and an objective lens of the inspecting optical system, based on the inspection treatment procedure designated in the step (A2), and
        collecting reflected light from the region irradiated with the inspection light, as a magnified image of the region, through the inspecting optical system; and
    (A4) a step of determining the rugged shape of the defect, from light intensity distribution of the magnified image, based on the criterion for determination designated in the step (A2).

2. The method of claim 1, wherein the step (A4) comprises:
    a treatment of comparing variation in light intensity level of a defect portion of the magnified image with light intensity level of a portion surrounding the defect; and
    a treatment of comparing the result of the comparing treatment with the criterion for determination.

3. The method of claim 1, wherein the distance in the step (A3) is a focus distance, and an inspection light application condition in the step (A3) is that the inspection light is non-polarized light.

4. The method of claim 1, wherein the inspection treatment procedure of the step (A2) includes a plurality of inspection conditions concerning the step (A3), and the step (A4) is conducted after the step (A3) is performed sequentially for all the inspection conditions included in the inspection treatment procedure.

5. The method of claim 4, wherein the plurality of inspection conditions include an inspection condition where the distance in the step (A3) is a focus distance and an inspection condition where the distance in the step (A3) is a defocus distance.

6. The method of claim 4, wherein the plurality of inspection conditions include:
    an inspection condition where the distance in the step (A3) is a focus distance;
    an inspection condition where the distance in the step (A3) is a positive defocus distance; and
    an inspection condition where the distance in the step (A3) is a negative defocus distance.

7. The method of claim 4, wherein the plurality of inspection conditions include:
    an inspection condition where an inspection light application condition in the step (A3) is that the inspection light is non-polarized light; and
    an inspection condition where an inspection light application condition in the step (A3) is that the inspection light is polarized light.

8. The method of claim 4, wherein the plurality of inspection conditions include:
    an inspection condition where an inspection light application condition in the step (A3) is that the inspection light is non-polarized light;
    an inspection condition where an inspection light application condition in the step (A3) is that the inspection light is transverse electric polarized light; and
    an inspection condition where an inspection light application condition in the step (A3) is that the inspection light is transverse magnetic polarized light.

9. The method of claim 3, wherein the plurality of inspection conditions include:
an inspection condition where the distance and an inspection light application condition in the step (A3) are a positive defocus distance and that the inspection light is transverse electric polarized light;
an inspection condition where the distance and an inspection light application condition in the step (A3) are a positive defocus distance and that the inspection light is transverse magnetic polarized light;
an inspection condition where the distance and an inspection light application condition in the step (A3) are a negative defocus distance and that the inspection light is transverse electric polarized light; and
an inspection condition where the distance and an inspection light application condition in the step (A3) are a negative defocus distance and that the inspection light is transverse magnetic polarized light, and wherein collection of a magnified image is conducted under each of the inspection conditions.

10. The method of claim 9, wherein the plurality of inspection conditions further include:
an inspection condition where the distance and an inspection light application condition in the step (A3) are a focus distance and that the inspection light is transverse electric polarized light; and
an inspection condition where the distance and an inspection light application condition in the step (A3) are a focus distance and that the inspection light is transverse magnetic polarized light.

11. The method of claim 5, wherein the step (A4) includes:

a treatment of calculating a minimum value of light intensity level of a defect portion of each magnified image; and
a treatment of comparing the result of the calculating treatment with the criterion for determination.

12. The method of claim 1, wherein the thin film is a hard mask film.

13. The method of claim 1, wherein the thin film has a thickness of up to 10 nm.

14. The method of claim 1, wherein the inspection light is light having a wavelength of 210 to 550 nm.

15. The method of claim 1, wherein the inspection light is applied by oblique illumination in which optical axis of the inspection light is inclined at a predetermined angle in relation to a normal to that surface of the thin film which is irradiated with the inspection light.

16. The method of claim 1, wherein in the step (A3), the photomask blank is placed on a stage which can be moved in an in-plane direction of the photomask blank, and the stage is moved in the in-plane direction to bring the defect and an objective lens of the inspecting optical system close to each other.

17. A method of sorting a photomask blank, comprising sorting out a photomask having no pit defect, based on rugged shapes of defects determined by the method of claim 1.

18. A method of producing a photomask blank, comprising:
a step of forming an optical thin film on a substrate and forming a thin film, as an outermost surface layer, on a side of the optical film opposite to the substrate; and
a step of determining rugged shape of a defect present in the thin film by the method of claim 1.

* * * * *